United States Patent [19]
Hastings et al.

[11] Patent Number: 5,873,835
[45] Date of Patent: Feb. 23, 1999

[54] INTRAVASCULAR PRESSURE AND FLOW SENSOR

[75] Inventors: Roger N. Hastings, Maple Grove; Paul T. Feld, Buffalo; Daniel M. Lafontaine, Plymouth; Kenneth R. Larson, Maple Grove; Richard R. Prather, Rogers, all of Minn.

[73] Assignee: Scimed Life Systems, Inc., Maple Grove, Minn.

[21] Appl. No.: 527,815

[22] Filed: Sep. 13, 1995

Related U.S. Application Data

[63] Continuation-in-part of Ser. No. 141,134, Oct. 22, 1993, Pat. No. 5,450,853, and a continuation-in-part of Ser. No. 304,565, Sep. 12, 1994, Pat. No. 5,617,870, which is a continuation-in-part of Ser. No. 55,702, Apr. 29, 1993, Pat. No. 5,346,508.

[51] Int. Cl.⁶ .................................................. A61B 5/0215
[52] U.S. Cl. ........................................... 600/488; 600/561
[58] Field of Search ..................... 128/672–675, 128/691–692, 748, 713, 634, 644–667, 633

[56] References Cited

U.S. PATENT DOCUMENTS

| 5,271,408 | 12/1993 | Breyer et al. |
|---|---|---|
| 5,284,138 | 2/1994 | Kujawski. |
| 5,333,609 | 8/1994 | Bedingham et al. |
| 5,450,853 | 9/1995 | Hastings et al. .................... 128/748 X |
| 5,595,182 | 1/1997 | Krivitski ................................. 128/692 |

*Primary Examiner*—Jeffrey R. Jastrzab
*Assistant Examiner*—Ryan Carter
*Attorney, Agent, or Firm*—Robert E. Atkinson

[57] ABSTRACT

An intravascular device for measuring blood pressure and flow is disclosed, which includes an elongate shaft having a pressure transducer and a flow transducer connected to its distal end. The pressure transducer may be a ferrofluid-type pressure transducer and the flow transducer may be an anemometer-type flow transducer. Measurement circuitry is also disclosed which provides a means for simultaneous measurement of both blood pressure and blood flow parameters. A sensor shield may be employed to isolate radial blood flow which is indicative of turbulent blood flow. An alternative blood flow measurement device is also disclosed which utilizes a thin metal film anemometer to measure flow in a vascular lumen.

25 Claims, 14 Drawing Sheets

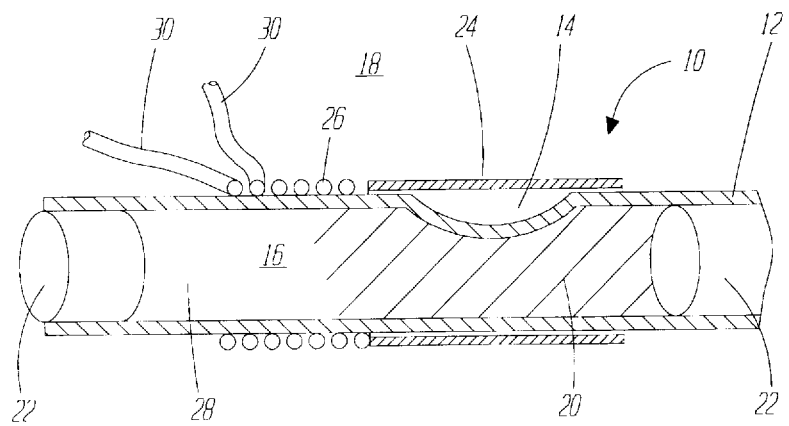
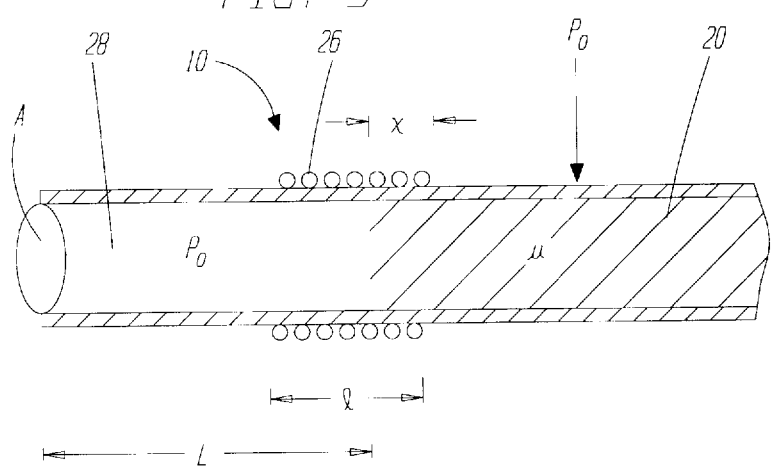
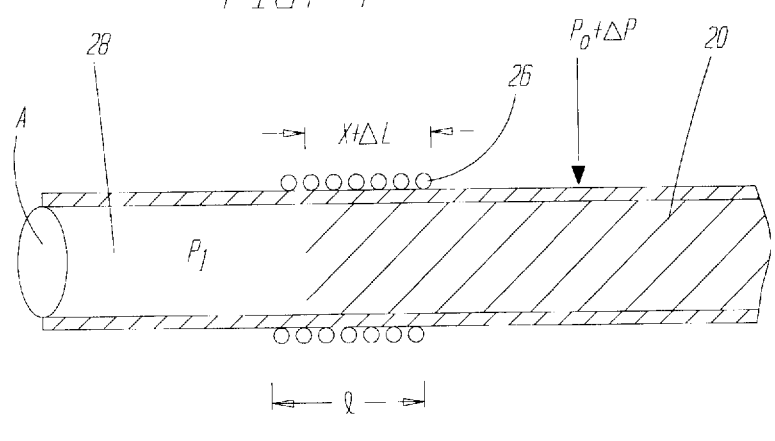

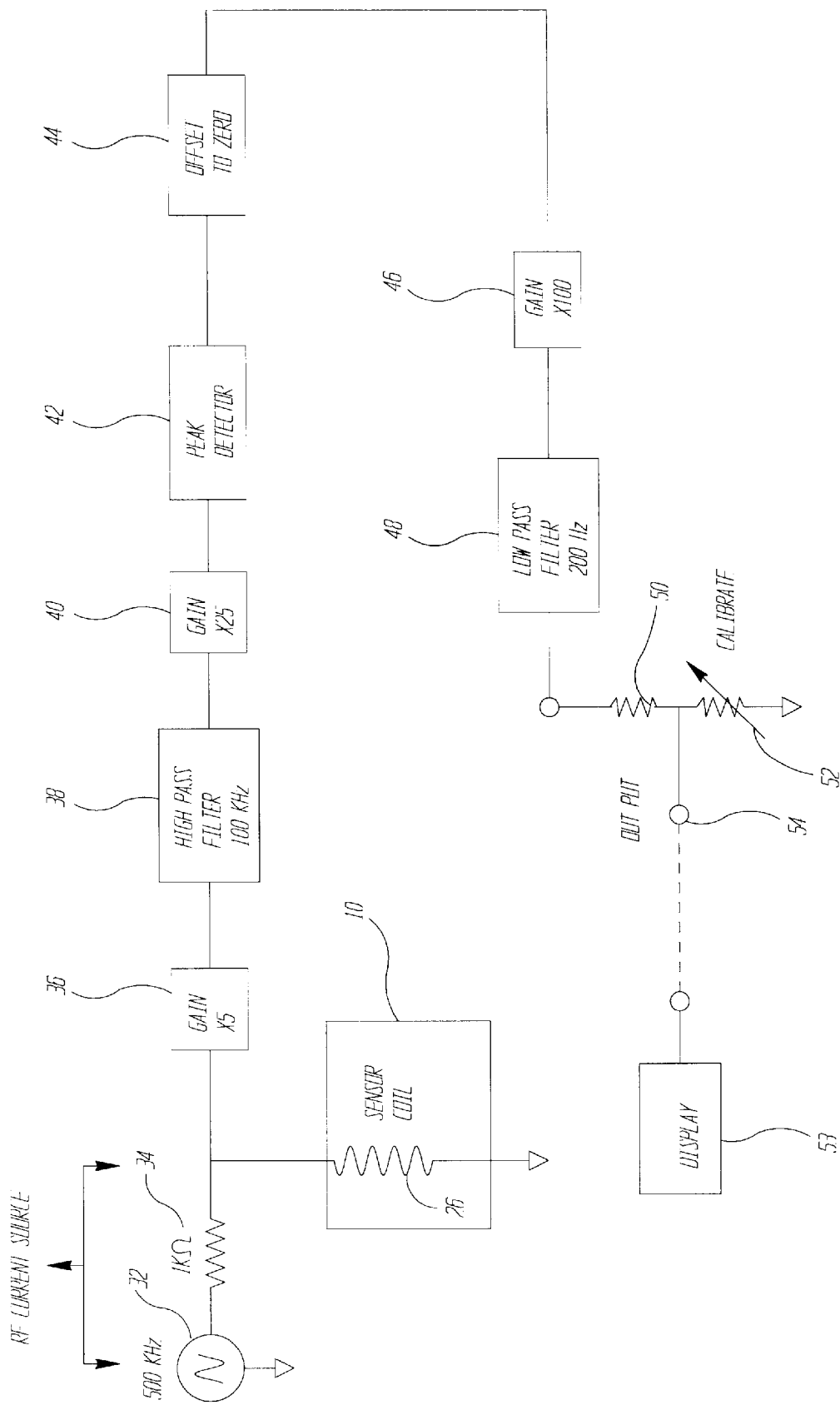

INTRAVASCULAR PRESSURE AND FLOW SENSOR

CROSS-REFERENCE TO RELATED APPLICATIONS

This case is a continuation-in-part of commonly assigned U.S. patent application Ser. No. 08/141,134, filed Oct. 22, 1993, now U.S. Pat. No. 5,450,853 and a continuation-in-part of Ser. No. 08/304,565, filed Sep. 12, 1994, now U.S. Pat. No. 5,617,870, which is a continuation-in-part of Ser. No. 08/055,702, filed Apr. 29, 1993, now issued as U.S. Pat. No. 5,346,508.

FIELD OF THE INVENTION

The present invention generally relates to intravascular medical devices used to measure blood flow and pressure. More specifically, the present invention relates to intravascular diagnostic devices used to measure blood flow and blood pressure in the coronary arteries. Those skilled in the art will recognize the benefits of applying the present invention to similar fields not discussed herein.

BACKGROUND OF THE INVENTION

Angioplasty procedures have gained wide acceptance in recent years as efficient and effective methods for treating types of vascular disease. In particular, angioplasty is widely used for opening stenoses in the coronary arteries, although it is also used for the treatment of stenoses in other parts of the vascular system.

The most widely used form of angioplasty makes use of a dilation catheter which has an inflatable balloon at its distal end. Inflation of the balloon at the site of the occlusion causes a widening of the lumen to reestablish an acceptable blood flow through the lumen.

Often it is desirable to determine the severity of the occlusion in order to properly choose a dilation catheter. Various techniques have been used to determine the severity of the occlusion. One way of determining the severity of the occlusion is to measure pressure both proximal to and distal of the stenosis. Devices that are used for this purpose include catheter-like members with some type of pressure-sensing device incorporated therein. One known device measures the pressure as a function of the deflection of a diaphragm located either the proximal or distal ends of the catheter. Positioning the sensing part of the sensing device at the proximal end of the catheter can introduce measuring inaccuracies due to the catheter length. Positioning the sensing part of the sensing device at the distal end of the catheter requires a sensing device to be made extremely small. Otherwise, the sensing device will impede the blood flow and affect the pressure reading. It is desirable to provide a pressure sensor that is compact so that it can be delivered to narrow sites while having a high degree of accuracy.

An alternative method of determining the severity of an occlusion is to measure blood flow proximal to, across and distal of the stenosis. Several techniques are in use to measure the flow of blood within a patient's vasculature. Doppler ultrasound and dilution techniques can be used to study blood flow in vessels. Hot wire anemometry has been proposed to measure blood flow as well.

The measurement of blood flow in a coronary artery is especially difficult due to the size and location of the vessel. For example, the measurement device must have a very small diameter so that the vessel under study is not occluded during the measurement. Occlusion will distort the flow measurement and can cause ischemia. It is also important that the flow measurement device generate a reproducible and accurate measure of blood flow as a function of time so that the pulsatile nature of the blood flow is revealed.

It would be desirable to make use of both measurement techniques in order to provide the treating physician with as much diagnostic information as possible. The ideal combined pressure and flow measurement apparatus would be accurate, low profile, flexible and have a fast response time. Both the cost and ease of use of the complete system needs to be considered as well to produce a commercially successful product. Presently available devices are not capable of simultaneously meeting these various requirements.

SUMMARY OF THE INVENTION

The present invention satisfies these unmet needs in a unique and creative manner. One embodiment of the present invention is an intravascular device which measures blood pressure and blood flow. The intravascular device includes an elongate shaft with a pressure transducer and a flow transducer connected to the distal end of the elongate shaft. The pressure transducer may include a column of ferrofluid which moves in response to changes in intravascular blood pressure. The pressure transducer may also include an electrically conductive coil surrounding the ferrofluid such that movement of the ferrofluid causes a change in inductance in the coil. The coil may be electrically coupled to an external measurement circuit which measures inductance of the coil as the ferrofluid moves in response to changes in intravascular blood pressure. The coil may also be supplied with an electrical current to heat the coil to a temperature above body temperature. The measurement circuit may then measure resistance of the coil as the resistance of the coil changes in response to intravascular blood flow. The measurement circuit may measure resistance and inductance simultaneously by utilizing such methods as frequency separation, phasic separation and computational analysis.

The present invention may also be described as an intravascular device for measuring blood pressure and flow where the device includes an elongate shaft having a ferrofluid-type pressure transducer and an anemometer-type flow transducer connected to the distal end of the elongate shaft.

Another embodiment of the present invention is a medical device for measuring blood flow in a vascular lumen where the device includes an elongate shaft with a first electrical path extending along its length. The first electrical path includes a short interruption near the distal end of the elongate shaft such that the interruption has a greater resistance per unit length than the resistance per unit length of the remainder of the electrical path. A second electrical path also extends with the elongate shaft and is connected to the first electrical path distal of the interruption. The first electrical path may be a thin metal film disposed on a polymer tube. The second electrical path may be a core wire extending inside the tube. The thin metal film may be about 10,000 to 400,000 Å thick and the interruption may be about 100 to 500 Å thick. The interruption may be about 0.02 to 0.50 inches wide. The tube may be made of a thin-walled polymer such as polyimide and the metal film may be coated on the tube. A portion of the metal film may be either disposed over the entire circumferential surface of the tube or over a portion of the circumferential surface of the tube.

Yet another embodiment of the present invention is a medical device for detecting turbulent blood flow, the device including a sensor and a sensor shield. The sensor shield surrounds the sensor to eliminate or reject blood flow which is essentially parallel (laminar flow) to the longitudinal axis of the sensor while allowing the radial (turbulent) flow to be detected. The sensor shield may comprise a tube having radially spaced holes and a proximal end sealed to the proximal end of the sensor. The tube may also have a distal end sealed to the distal end of the sensor.

BRIEF DESCRIPTION OF THE DRAWINGS

FIGS. 1–8 illustrate a pressure measurement system of the present invention.

In particular, FIG. 1 illustrates a cross-sectional view of a first embodiment of a pressure sensor according to the present invention.

FIG. 2 illustrates in schematic the electronics used in conjunction with the pressure sensors of the present invention.

FIG. 3 illustrates a schematic of the pressure sensor at an initial condition where the sensor is exposed to ambient pressure.

FIG. 4 illustrates a schematic of the pressure sensor exposed to an external pressure.

FIG. 5 illustrates a cross-sectional view of the pressure sensor of FIG. 1 incorporated into a guide wire.

FIG. 6 illustrates in further detail a portion of the guide wire shown in FIG. 5.

FIG. 7 illustrates a schematic of a pressure sensor according to another embodiment of the present invention.

FIG. 8 illustrates a cross-sectional view of the pressure sensor of FIG. 7 incorporated in a guide wire.

FIG. 9 is a schematic view of the flow measurement system.

FIG. 10 is a guide wire incorporating the intravascular flow measurement device.

FIG. 11 is a perfusion catheter incorporating the intravascular flow measurement device.

FIG. 12 is a schematic diagram of a representative implementation of the flow measurement system.

FIG. 13 illustrates a side view of a first embodiment of a combined pressure and flow sensor according to the present invention.

FIG. 14 illustrates a break-away view of the distal end of the combined pressure and flow measurement system depicted in FIG. 13.

FIG. 15 illustrates a second break-away view of the distal end of the combined pressure and flow measurement system depicted in FIG. 13.

FIG. 16 illustrates a block diagram of the frequency separation circuitry used to measure blood pressure and blood flow simultaneously.

FIG. 17 illustrates a block diagram of phasic separation circuitry used to measure blood pressure and blood flow simultaneously.

FIG. 18 illustrates a block diagram of computational separation circuitry used to measure blood flow and blood pressure simultaneously.

FIG. 19 illustrates a side cross-sectional view of an alternate embodiment of a flow sensor incorporated into a guide wire.

DETAILED DESCRIPTION OF THE INVENTION

Figure 5:
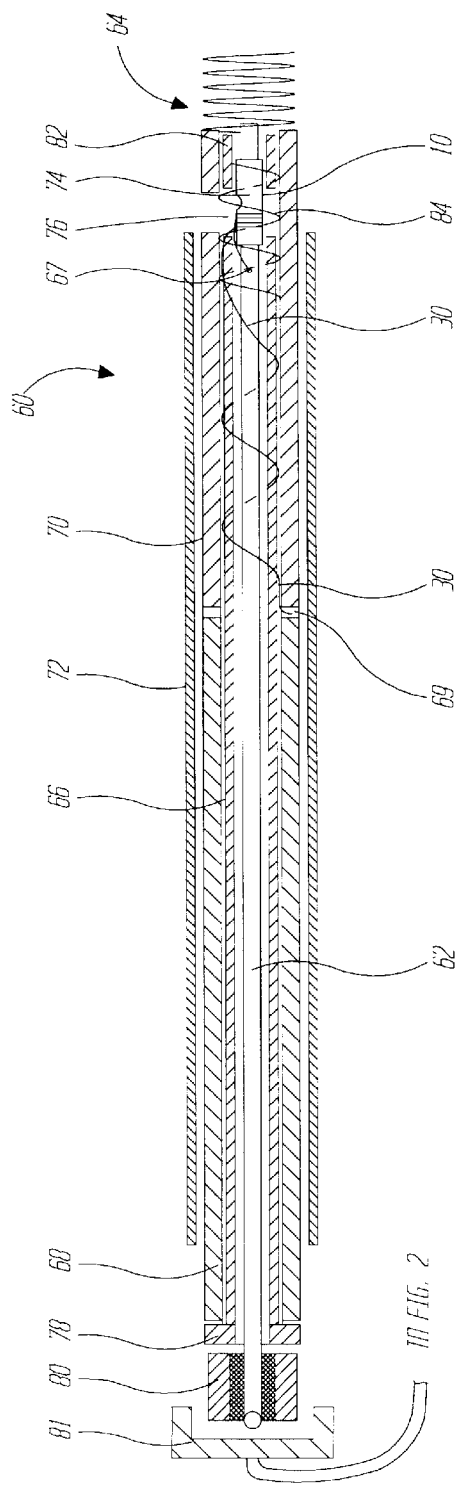

The following detailed description should be read with reference to the drawings in which like elements in different figures are numbered identically.

Specific materials, dimensions and manufacturing processes are provided for selected design elements. Those design elements which do not have specific materials, dimensions or manufacturing process identified, employ that which is well known to those skilled in the field of the invention. In addition, those skilled in the art will recognize many of the materials, dimensions and manufacturing processes identified are exemplary, for which suitable alternatives may be utilized.

Pressure Measurement Embodiment

Refer first to FIGS. 1–8 which illustrate a pressure measurement system of the present invention. FIG. 1 illustrates a cross-sectional view of a first embodiment of a pressure sensor according to the present invention. The pressure sensor 10 includes a tubular member 12 having a window or opening 14 cut out of one side. The window 14 exposes the interior 16 of the tube to the exterior 18 of the tube. A portion of the interior 16 of the tubular member 12 is filled with a ferrofluid column 20 and the remainder is filled with air. Each end of the tubular member is sealed with a plug 22 to create a closed volume within the interior of the tubular member 12. A sheath 24 surrounds a portion of the exterior 18 of the tubular member 12. In particular, the sheath 24 completely covers the window 14 formed in the tubular member 12. A coil 26 is wound around a portion of the exterior 18 of the tubular member 12. The coil 26 is located proximal to the sheath 24. The coil 26 has leads 30 which are used to connect the coil 26 to an electronic circuit which will be described in detail with reference to FIG. 2. As previously described, the ferrofluid column 20 fills a portion of the interior of the tubular member 12 and the remainder of the closed volume is filled with air, creating an air column 28.

In a preferred embodiment, the various pieces of the sensor 10 are formed of the following materials and have the following dimensions. Other materials and different dimensions may be used not only in the presently-described embodiment, but in all embodiments of the present invention. The present invention is not limited to the disclosed materials or dimensions. The tubular member 12 is formed from a polyimide tube having a length of about 0.2 inches, an outer diameter of about 0.0071 inches and an inner diameter of about 0.0056 inches. The sheath 24 is formed of polyester having a length of about 0.075 inches and a thickness of about 0.00018 inches. The coil 26 is formed of 50-gauge insulated silver wire wound in two layers having 80 turns per layer to create a coil length of about 0.1 inches. The sensor 10 has a maximum outer diameter located at the coil 26 of about 0.011 inches. The plugs 22 are formed of nickel titanium (NiTi) and have a diameter of about 0.005 inches which allows the plugs 22 to securely seal the ends of the tubular member 12. The ferrofluid column 20 occupies a volume of about $4 \times 10^{-6}$ cubic inches and has a length of about 0.15 inches. Ferrofluid, as those skilled in the art know, is a suspension of iron filings. Preferably, the ferrofluid 20 used is commercially available from Ferrofluidics of Nashua, N.H. Preferably, part TPG 14 is used because it has a low viscosity and a high magnetic permeability. The operation of the sensor will be described after the electronics have been described.

FIG. 2 illustrates in schematic the electronics used in conjunction with the sensors of the present invention. The electronics include a variable frequency generator 32 connected to one end of a resistor 34. The other end of the resistor 34 is connected to the coil 26 of the sensor 10, represented in schematic as a block, via the coil leads 30 and to an input of a gain circuit 36. The output of the gain circuit 36 is connected to a high pass filter 38 which is connected to another gain circuit 40. The output of the gain circuit 40 is connected to a peak detector circuit 42. The output of the peak detector circuit 42 is connected to an offset circuit 44 and the output of the offset circuit 44 is connected to the input of another gain circuit, 46. The output of the gain circuit 46 is applied to the input of a low pass filter 48. The output of the low pass filter 48 is connected to ground through a resistor 50 and a potentiometer 52. An output 54 is taken after the resistor 50 but before the potentiometer 52. The output 54 is connected to a display device 53.

In a preferred embodiment, the variable frequency generator generates an alternating current signal having a frequency of about 500 kiloHertz (kHz). The resistor 34 is about 200 Ohm ($\Omega$) to 1 kOhm (k$\Omega$), the resistor 50 is about 100 k$\Omega$ and the potentiometer has a maximum resistance of about 100 k$\Omega$. Gain circuit 36 has a gain of about 5, gain circuit 40 has a gain of about 25 and gain circuit 46 has a gain of about 100. The high pass filter 38 has a corner frequency of about 100 kHz and the low pass filter has a corner frequency of about 200 Hertz (Hz). The display device 53 can be in the form of an oscilloscope, voltmeter, graphics display, chart recorder or any other type of display or peripheral device that would be helpful to the user of the sensor. The voltage measured across the coil of the sensor is thus converted by the circuitry of FIG. 2 to provide a pressure measurement. The components forming the electronics of the present invention are formed from conventional devices well known to those skilled in the art and thus need not be described in greater detail. Of course, the electronics shown in FIG. 2 would be contained in a suitable housing.

The principle of operation of the pressure sensor of FIG. 1 in combination with the electronics of FIG. 2 will now be described. Thereafter, other embodiments of the pressure sensor will be described with reference to FIGS. 5–8. FIG. 3 illustrates a schematic of the pressure sensor at an initial condition where the sensor is exposed to ambient pressure $P_0$. While the window 14 of the sensor has not been illustrated, exerted pressure $P_0$ is shown acting on the pressure sensor where the window would be located. The proximal interior of the sensor is filled with a column of air 28, having length L, and a cross section A. The air column 28 is at ambient pressure $P_0$. The remaining distal portion of the sensor is filled with the ferrofluid column 20 having a permeability of $\mu$. The coil 26 has a length l comprised of N turns. The coil is positioned so that a distal length x surrounds the ferrofluid column 20. Initially, the inductance in the coil $L_0$ is described by equation (1);

$$L_0 = \mu_0 \mu N^2 (Ax/l), \tag{1}$$

where $\mu_0$ is the permeability of free space.

The pressure $P_0$ in the air column is described by the gas law equation (2);

$$P_0 = CT/V = CT/AL, \tag{2}$$

where V is the volume of the air column 28, C is a constant and T is temperature in degrees Kelvin.

When an external pressure, $P_0+\Delta P$, is exerted at the window of the sensor 10, the ferrofluid column 20 is displaced a distance $\Delta L$ in the proximal direction. FIG. 4 illustrates a schematic of the pressure sensor exposed to such an external pressure. The displacement of the ferrofluid column causes an equal displacement of the air column 28 thereby increasing the pressure of the air column 28. The window material is chosen so that force exerted on the ferrofluid column by the compressed air column is much larger and dominates the elastic restoring force of the window. From equation (2), increased pressure $P_1$ of the air column 28 is described by equation (3).

$$P_1 = CT/(A(L-\Delta L)) \tag{3}$$

By making the approximation that the ratio of $\Delta L$ to L is much less than 1 (i.e. $\Delta L/L \ll 1$), equation (3) can be reduced to equation (4).

$$P_1 = P_0 + P_0(\Delta L/L) = P_0 + \Delta P \tag{4}$$

From equation (4) it is apparent that the ratio of $\Delta L$ to L is approximately the same as the ratio of $\Delta P$ to $P_0$ (i.e. $\Delta L/L = \Delta P/P_0$).

Inductance in the coil is described by equation (6);

$$L = \mu_0 \mu N^2 (A/l)(Z/l), \tag{6}$$

where Z equals the length of ferrofluid column surrounded by the coil. With reference to FIG. 4, Z equals $x+\Delta L$ and the inductance of the coil is described by equation (7).

$$L = \mu_0 \mu N^2 (A/l)((x+\Delta L)/l) \tag{7}$$

Using equation (1), equation (7) can be reduced to equation (8).

$$L = \zeta_0 + \zeta_0 (\Delta L/l) = L_0 + L_0 (L/l)(\Delta P/P_0) \tag{8}$$

The voltage across the coil 26 for a constant drive current I is measured by the electronics of FIG. 2. For a constant current I applied to the coil, the voltage across the coil is described by equation (9).

$$V = I\sqrt{R^2 + \omega^2 L^2}, \tag{9}$$

where $\omega$ is equal to $2\pi \times$ the frequency of the signal applied by generator 32 of FIG. 2, R is the resistance of the coil and L is the inductance of the coil. Thus the voltage is dependent upon both the resistance of the coil and its inductance.

Substituting equation (8), equation (9) is described by equation (10).

$$V = I\sqrt{R^2 + \omega^2 L^2_o} \ (1 + (\omega^2 L^2_o/(R^2 + \omega^2 L^2_o))(L/l)(\Delta P/P_o)) \tag{10}$$

Eliminating the offset represented by the term $$I\sqrt{R^2 + \omega^2 L^2_o}$$

the change in voltage, $\Delta V$, is described by equation (11).

$$\Delta V = \left(\left(I\omega^2 L^2_o/\sqrt{R^2 + \omega^2 L^2_o}\right)(L/l)(\Delta P/P_o)\right) \tag{11}$$

From equation (11) it can be seen that the change in voltage, $\Delta V$, is linearly proportional to the change in pressure $\Delta P$. In summary, an alternating current is passed through the coil of the sensor and the voltage across the coil is monitored. Physiologic pressure variations result in proportional variations in the position of the ferrofluid column relative to the coil. This results in proportional changes in the coil voltage due to the change in the coil's inductance caused by the movement of the ferrofluid column.

Changes in temperature, otherwise known as temperature drift, affect both the resistance and inductance of the coil and thus affect the measured voltage across the coil. To compensate for the effects of temperature drift, the following adjustments are made which virtually eliminate the effects of temperature drift on the voltage measured across the coil. It has been found that the effects of temperature change on the resistance and the inductance of the coil are opposite. That is to say, as one increases the other decreases and vice versa. The effect of temperature change is described by equation (12).

$$dV/dT = I((dV/dR)(dR/dT) + (dV/dL)(dL/dT)) \quad (12)$$

Using equation (9), equation (12) is expanded to equation (13).

$$dV/dT = \left(IR/\sqrt{R^2 + \omega^2 L^2}\right)(dR/dT) + \left(\left(I\omega^2 L/\sqrt{R^2 + \omega^2 L^2}\right)(dL/dT)\right) \quad (13)$$

Because the coil is preferably formed of a silver wire, the term dR/dT is a positive constant. In addition, using equation (6), the term dL/dT can be described by equation (14):

$$dL/dT = L_0(1/x)(dx/dT) = -L_0(1/x)(dL/dT) \quad (14)$$

Using the gas law of equation (2), equation (14) is further reduced to equation (15).

$$dL/dT = (-L_0/T)(L/x) \quad (15)$$

Using equation (15), equation (13) is reduced to equation (16).

$$dV/dT = \left(IR/\sqrt{R^2 + \omega^2 L^2}\right)[(dR/dT) - (\omega^2 L^2/R)(L/x)(1/T)] \quad (16)$$

The frequency, $\omega$, of generator 32 is adjusted to yield a zero drift (i.e., dV/dT=0), or stated differently $dR/dT = ((\omega L)^2/(RT))(L/x)$ or $(\omega L/R)^2 = (x/L)(T/R)(dR/dT)$.

For silver, the term (1/R) (dR/dT) is equal to about 0.0038/° K, body temperature is about 310° K and x/L is approximately 0.5. Thus $\omega L/R$ is equal to about 0.8. In a preferred embodiment, R is about 6Ω and L is about 1.5 μH. Since $\omega = 2\pi f$ where f is frequency in Hertz, we find f is about equal to 510 kHz which is close to the experimentally found frequency at which the sensor thermal drift is equal to zero.

In summary, R increases with an increase in temperature while L decreases with an increase in temperature because as the temperature increases, air column 28 expands and pushes the ferrofluid column distally out from under the coil 26. The impedance of the coil is resistive at low frequencies and inductive at high frequencies. Thus a frequency exists for which the resistive and inductive thermal drifts cancel to zero.

FIG. 5 illustrates a cross-sectional view of the pressure sensor of FIG. 1 incorporated in a guide wire 60. According to this embodiment, the guide wire 60 includes a core wire 62, a spring tip 64 having an extension member 74, a first sheath 66, a first tubular member 68, a second tubular member 70, a second sheath 72, a third sheath 82 and a coil 84. The pressure sensor 10 is located between the distal end of the core wire 62 and the proximal end of the extension member 74. In a preferred embodiment, neither the distal end of the core wire 62 nor the proximal end of the extension member 74 are physically joined to the sensor 10.

Surrounding and in contact with approximately the entire length of the core wire 62 is the first sheath 66. Surrounding and in contact with the extension member 74 is the third sheath 82. Surrounding a proximal portion of the core wire 62 and the first sheath 66 is the first tube 68. The proximal end of the second tube 70 is bonded to the distal end of the first tube 68 so that the second tube 70 surrounds the distal portion of the core wire 62, sensor 10, coil 84 and extension member 74. The second tubular member 70 has a window or opening 76 cut out on one side to expose the sensor 10 as will be described in detail hereinafter. The spring tip 64 is located distal to the distal end of the second tubular member 70. Surrounding and in contact with most of the first and second tubular members, 68 and 70, is the second sheath 72. Preferably, the second sheath terminates at the window 76 formed in the second tubular member 70.

Figure 6:
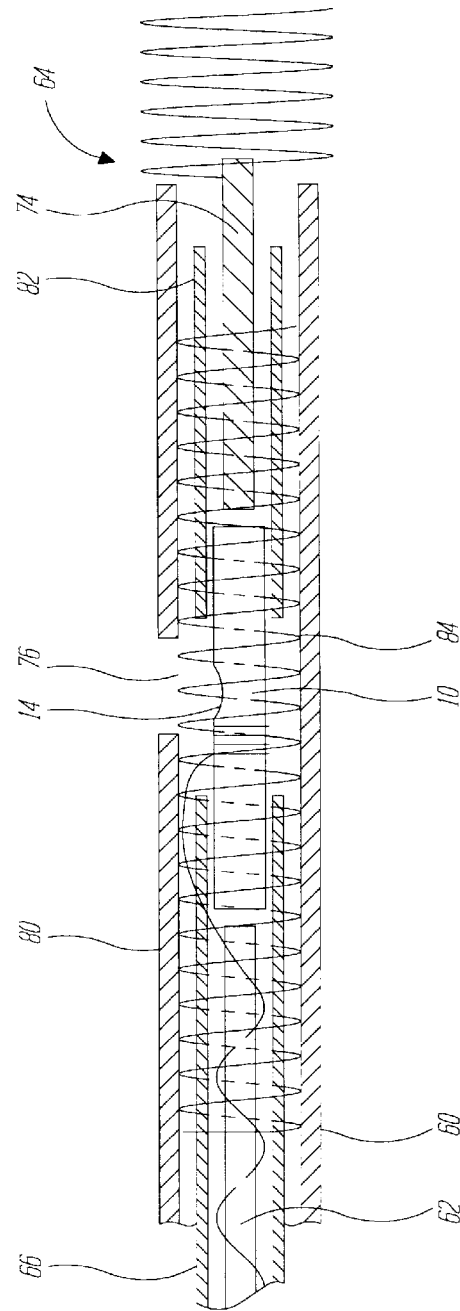

The coil 84 surrounds the sensor and a portion of the first sheath 66 and the third sheath 82. A more detailed illustration of this section of the guide wire is shown in FIG. 6 and will be described hereinafter.

The proximal end of the spring tip 64 is bonded to extension member 74 preferably by soldering. One lead 30 of the coil 26 is soldered to the core member 62 at 67. The second lead 30 is wrapped around the exterior of the first sheath 66 and is soldered at 69 to the distal end of the first tubular member 68.

At the proximal end of the first tubular member is an insulating spacer 78 bonded to the proximal end of the first tubular member 68 and the first sheath 66. Proximal to the insulating spacer 78 is a third tubular member 80. The third tubular member 80 is connected to the proximal portion of the core wire 62 preferably by a conductive epoxy.

In a preferred embodiment, the various components of guide wire 60 are formed from the following materials and have the following dimensions. Core wire 62 is formed from a gold plated stainless steel wire having a length of about 66 inches and a diameter of about 0.008 inches. The first sheath 66 is formed from an insulating material, preferably polyimide or polyester and has a length of about 65 inches. First tubular member 68 is formed of gold plated stainless steel tubing having a length of about 59 inches, an inner diameter of about 0.012 inches and an outer diameter of about 0.017 inches. The second tubular member 70 is formed from polyester or a blend of nylon and polyether or polyether block amide, commercially available under the tradename PEBAX from Autochem of Birdsboro, Pa. The second sheath 72 may be formed of polyester or alternatively, TEFLON may be coated over the first and second tubular members 68 and 70. The third tubular member 80 is formed by a gold plated stainless steel tube and has a length of about 1.0 inches, an inner diameter of about 0.012 inches and an outer diameter of about 0.017 inches.

As previously described, the leads 30 of sensor coil 26 are soldered to the core member 62 at 67 and first tubular member 68 at 69. Because the core member 62 and the first tubular member 68 are formed of gold plated stainless steel, they act as conductors which extend the leads to the proximal end of the guide wire. The proximal end of the first tubular member 68 and the third tubular member 80, separated from the first tubular member 68 by insulating spacer 78, are then used as contact points. A connector (not shown) is attached to the proximal end of the guide wire and the connector makes contact with the third tubular member 80 and the proximal end of the first tubular member 68. The connector connects the guide wire to the electronics of FIG. 2. Alternatively, the leads 30 may be extended the length of the guide wire to the guide wire's proximal end by any of the techniques described in U.S. Ser. No. 08/055,702, filed Apr. 29, 1993 entitled "Apparatus and Method For Performing Diagnostics and Intravascular Therapies" and U.S. Ser. No. 07/969,743, filed Oct. 30, 1992 entitled "Vibration Sensing Guidewire," the entire disclosures of which are hereby specifically incorporated by reference.

Delivery of a guide wire to the site of an occlusion is well known by those skilled in the art and thus need not be described in detail. The guide wire 60 of FIG. 5 is delivered so that the window 76 formed in the second tubular member 70 is positioned proximal to the occlusion to expose the sensor 10 to the pressure existing in the vessel or artery at that location. The guide wire 60 is then moved to a location distal to the occlusion to measure the pressure at that location.

FIG. 6 illustrates in further detail a portion of the pressure sensor of FIG. 5. The third sheath 82 surrounds and contacts a portion of the sensor 10 distal to the sensor's window 14 and most of the extension member 74. Coil 84 surrounds the sensor 10 and extends both proximally and distally of the sensor to surround a portion of the first sheath 66 and a portion of the third sheath 82. In a preferred embodiment, the third sheath 82 is formed of polyimide and has a length of about 0.5 inches, an inner diameter of about 0.008 inches and an outer diameter of about 0.010 inches. Coil 84 is formed of stainless steel wire having a diameter of about 0.002 inches and the coil 84 has a length of about 1.0 inches formed by 200 turns.

The coil 84 is provided for support over the sensor 10 to reduce forces that may be applied to the sensor 10 as the guide wire 80 is being delivered intravascularly.

Figure 7:
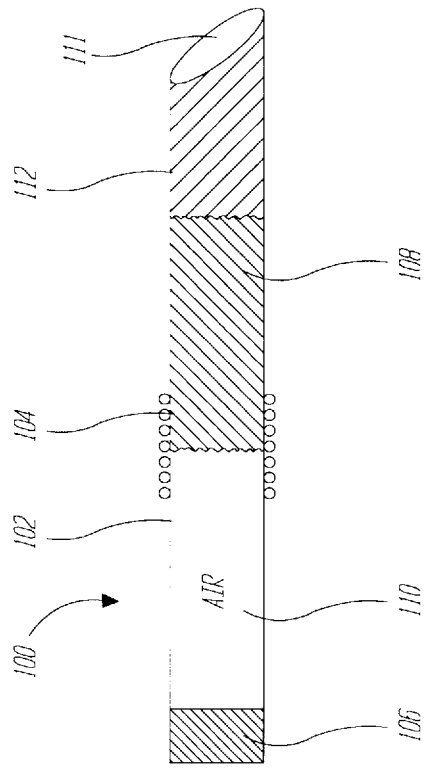

FIG. 7 illustrates a schematic of a pressure sensor 100 according to another embodiment of the present invention. The pressure sensor 100 includes a tubular member 102, a sensor coil 104 and a plug 106. The plug 106 is inserted into the proximal end of the tubular member 102 to securely seal that proximal end. A distal portion of the interior of the tubular member 102 is filled with a ferrofluid column 108 while the proximal portion of the interior of the tubular member 102 is filled with air creating an air column 110. Unlike the sensor of FIG. 1, a window is not provided in the side of the tubular member 102 but rather the window 111 is formed by leaving the distal end of the tubular member 102 open. Tubular member 102 is preferably a metalized polyimide tube available form HV Technologies, Inc. located in Trenton, Ga.

As stated previously, the preferred ferrofluid is commercially available from Ferrofluidics of Nashua, N.H. Preferably, part TPG 14 is used because it has a low viscosity and a high magnetic permeability. TPG 14 is non-toxic and nonvolatile. Other suitable ferrofluids may be employed such as part EMG 905 commercially available from Ferrofluidics of Nashua, N.H. EMG 905 has a low viscosity and a high magnetic permeability but is volatile.

If a volatile ferrofluid is used, it may be necessary to use a non-volatile fluid 112 to act as a plug similar to the plug 106 at the proximal end of the sensor to prevent the evaporation of the ferrofluid when the sensor is not in use. The non-volatile fluid 112 fills the distal most portion of the interior of the tubular member between the ferrofluid column 108 and the window 111 formed by the open distal end of the tubular member. In a preferred embodiment, the non-volatile fluid used is dioctylphthalate available from the Aldrich Chemical Company of Milwaukee, Wis. Apart from the described differences in construction, the pressure sensor 100 operates in a similar manner as previously described with reference to the other sensors.

Figure 8:
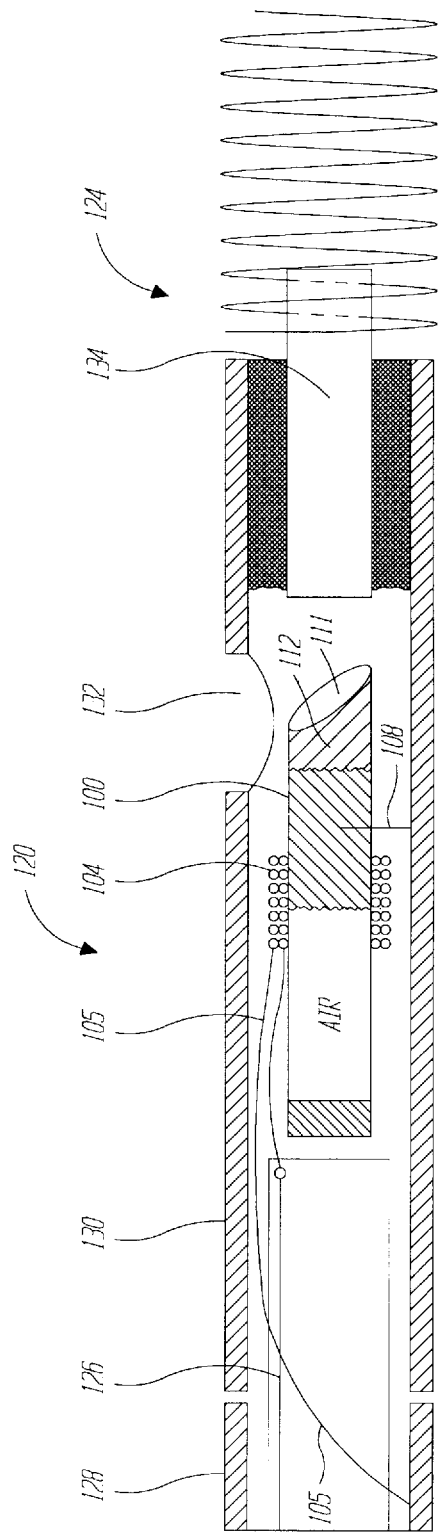

FIG. 8 illustrates a cross-sectional view of the sensor of FIG. 7 incorporated in a guide wire 120. The guide wire 120 includes a core wire 122, a spring tip 124, a sleeve 126, a first tubular member 128 and a second tubular member 130. The second tubular member has a window or opening 132 cut out on one side. In a preferred embodiment, the materials and dimensions of the various components forming the guide wire 120 are as follows. The core wire 122 is formed of a gold plated stainless steel core wire and has a diameter of about 0.007 inches and a length of about 66 inches. The sleeve 126 is formed of an insulating material, preferably polyimide, and has a length of about 65 inches. The first tubular member is formed of a plastic and has a length of about 6 inches, an inner diameter of about 0.008 inches and an outer diameter of about 0.017 inches. The second tubular member 130 is formed of stainless steel and has a length of about 1.0 inches, and inner diameter of about 0.012 inches and an outer diameter of about 0.017 inches.

The proximal end of the sensor 100 and the distal end of the core wire 122 are brought in close proximity but preferably are not connected or coupled to one another. The sleeve 126 surrounds and contacts the exterior surface of the core wire 122. The first tubular member 128 surrounds but does not contact a proximal portion of the core wire 122 and sleeve member 126. The second tubular member 130 surrounds the distal portion of the core wire 122 and sleeve 126, the pressure sensor 100 and the extension member 134 of the spring tip 124. An adhesive bonds the extension member 134 of the spring tip 124 in the distal end of the second tubular member 130 so that the coils of the spring tip 124 extend distally from the distal end of the second tubular member 130. A close tolerance fit exists between the exterior of the sensor 100 and the interior of the second tubular member 130 so that the second tubular member 130 keeps the sensor 100 in position. Because the sensor is not coupled or connected to any other elements of the guide wire 120, the forces exerted on it are lessened as the guide wire is delivered to the site of the occlusion.

The leads 105 of the coil 104 are connected to the core wire 122 and first tubular member 128 as was previously described with reference to FIG. 5.

The guide wire 120 is delivered to the occlusion so that the window 132 formed in the second tubular member 130 exposes the sensor 100 to the pressure existing in the vessel or artery proximal to the occlusion and then the guide wire is moved to position the window at a location distal to the occlusion to measure the pressure at that location.

In another embodiment of the present invention, the non-volatile liquid interface 112 of FIG. 7 may be replaced with a water soluble polymer such as polyehthleneoxide available from the Aldrich Chemical Company of Milwaukee, Wis. The water soluble polymer hardens when it is placed in the tubular member of the sensor and thus forms an interface between the ferrofluid and the environment in which the sensor is placed thus preventing evaporation of the ferrofluid. When used in a patient, the water soluble polymer dissolves and the sensor becomes functional. As an alternative, it would also be preferable to use a ferrofluid which is non-volatile and non-toxic which would obviate the need for the non-volatile or water soluble plugs.

While the sensor has been illustrated as incorporated into guide wires, the pressure sensors 10 and 100 of FIGS. 1 and 7 respectively, may be incorporated into other devices and the present invention is not limited to the devices illustrated.

Flow Measurement Embodiment

Figure 9:
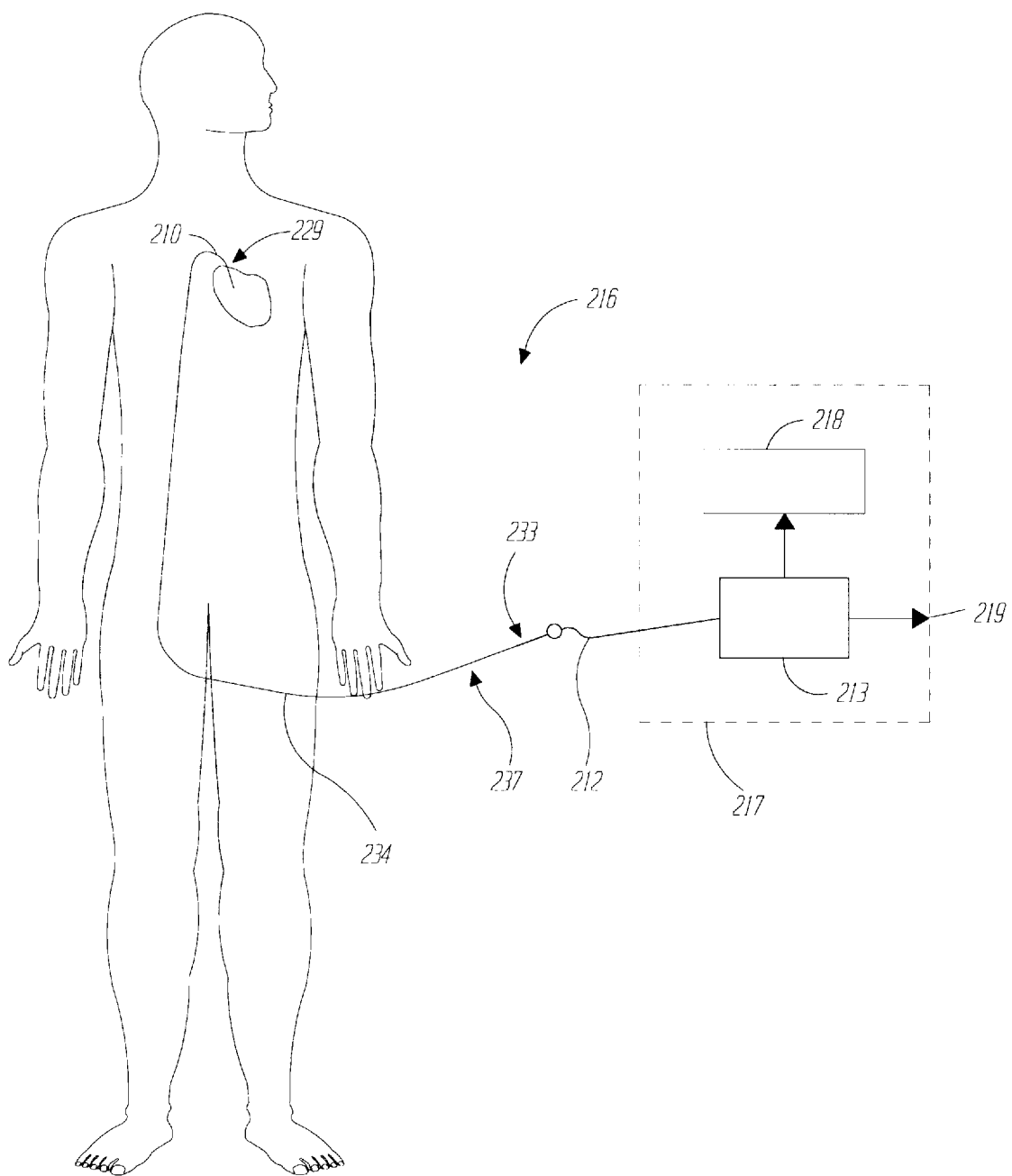
FIGS. 9–12 illustrate a flow measurement system of the present invention.

Refer now to FIGS. 9–12 which illustrate a flow measurement system of the present invention. FIG. 9 shows an intravascular flow measurement system 216. The intravascular flow measurement device 210 is positioned in a coronary artery in the patient's body. The intravascular flow measurement device 210 has a distal end 229 and a proximal end 233. The intravascular flow measurement device 210 is located within a sheath 234 which has a distal end 235 and a proximal end 237. An appropriate cable 212 is used to couple the sensor coil 230 of the intravascular flow measurement device 210 to a calibration and display system 217. The calibration and display system 217 includes an electronic circuit 213 which is coupled to an output terminal 219 and a data display 218.

In this specific flow measurement situation, the physician has passed the intravascular flow measurement device 210 through the guide catheter or sheath 234 to the desired anatomic site. Next, the physician will manipulate the proximal end 233 of the intravascular flow measurement device 210 to position both the sheath 234 and the sensor coil 230 with respect to the blood flow at the selected site. In use, the physician will manipulate the measurement device 210, the sheath 234 and several controls on the calibration display system 217. Typically, a physician will observe the pulsatile blood flow on a laboratory monitor connected to output terminal 219 and observe average flow data on an appropriate data display 218 which is integrated into the calibration and display system 217.

Figure 10:
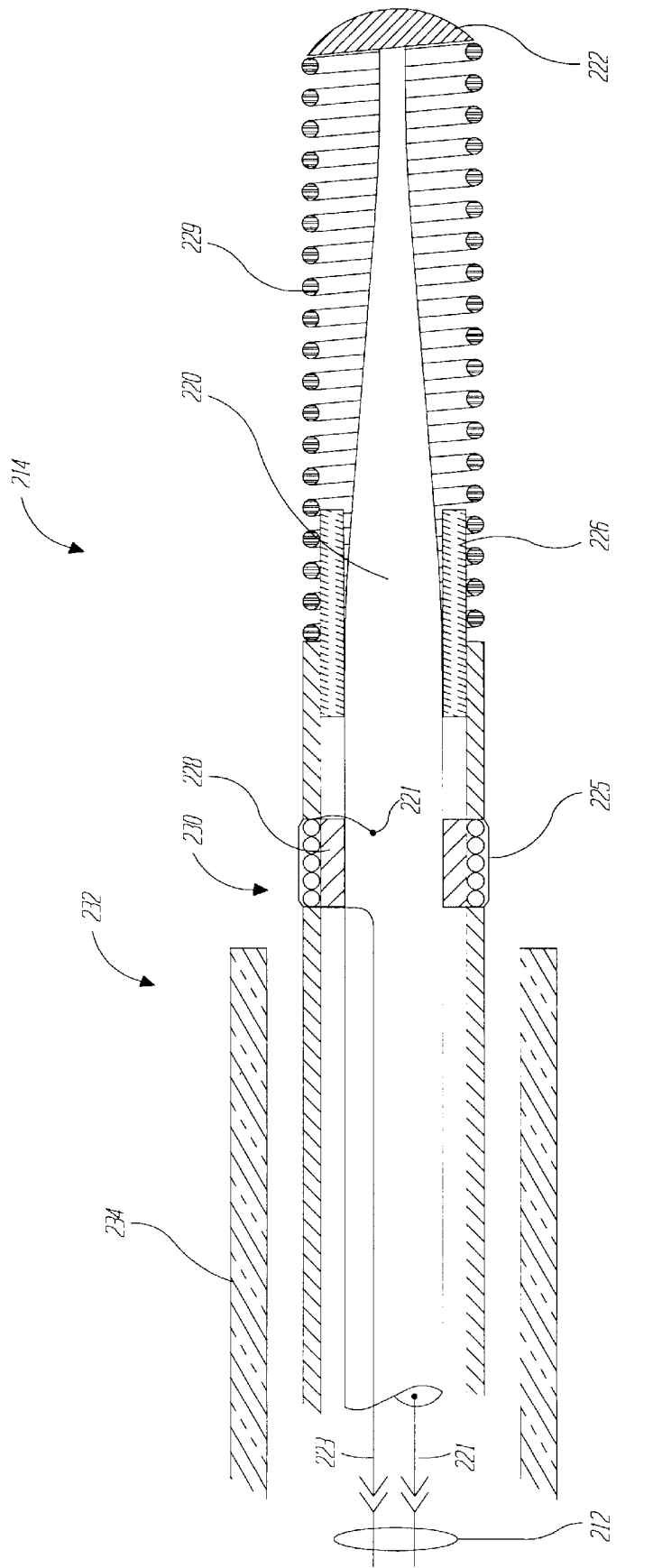

FIG. 10 shows an intravascular flow measurement device 210 incorporated into the distal end 229 of the guide wire 214. The guide wire 214 includes a wire core 220 which terminates in a distal tip 222. A spring coil 224 surrounds the wire core 220 and is attached to both the distal tip 222 and to an anchor ring 226. The guide wire core 220 may be made of any appropriate material such as stainless steel. However, to reduce the resistance of the electrical connections to the sensor coil 230, it is desirable to plate the wire core 220 with gold or silver to electrically couple the sensor coil 230. The sensor coil 230 is mounted on an insulating spacer 228 which thermally and electrically isolates the sensor coil 230 from the wire core 220. The sensor coil 230 is preferably wound as a bifilar helix around the insulating spacer 228. One lead 221 of the sensor coil 230 is electrically connected to the plated surface of the wire core 220 while the other lead 223 extends from the proximal end of the guide wire 214. These two leads are connected via an appropriate cable 212 to the calibration and display system 217. A hydrophilic slip coat or silicone slip coat 225 is applied onto the exterior of the guide wire to facilitate use of the wire. Coatings of this type prevent blood from coagulating on the sensor coil 230. These coatings are also an aid to repositioning the measurement device 210 both within the lumen 227 on the sheath 234 and within the vasculature.

In the Figure, the sensor 230 is shown proximate the distal end 232 of a guide catheter or therapy selection sheath 234. In use, the physician retracts a sensor coil 230 a short distance into the lumen 227 of the sheath 234. Temperature and quiescent current measurements are made at this calibration site. Next, the sensor coil 230 is advanced out of the sheath 234 to a measurement site where it is exposed to blood flow and the dynamic flow measurements are made.

Figure 11:
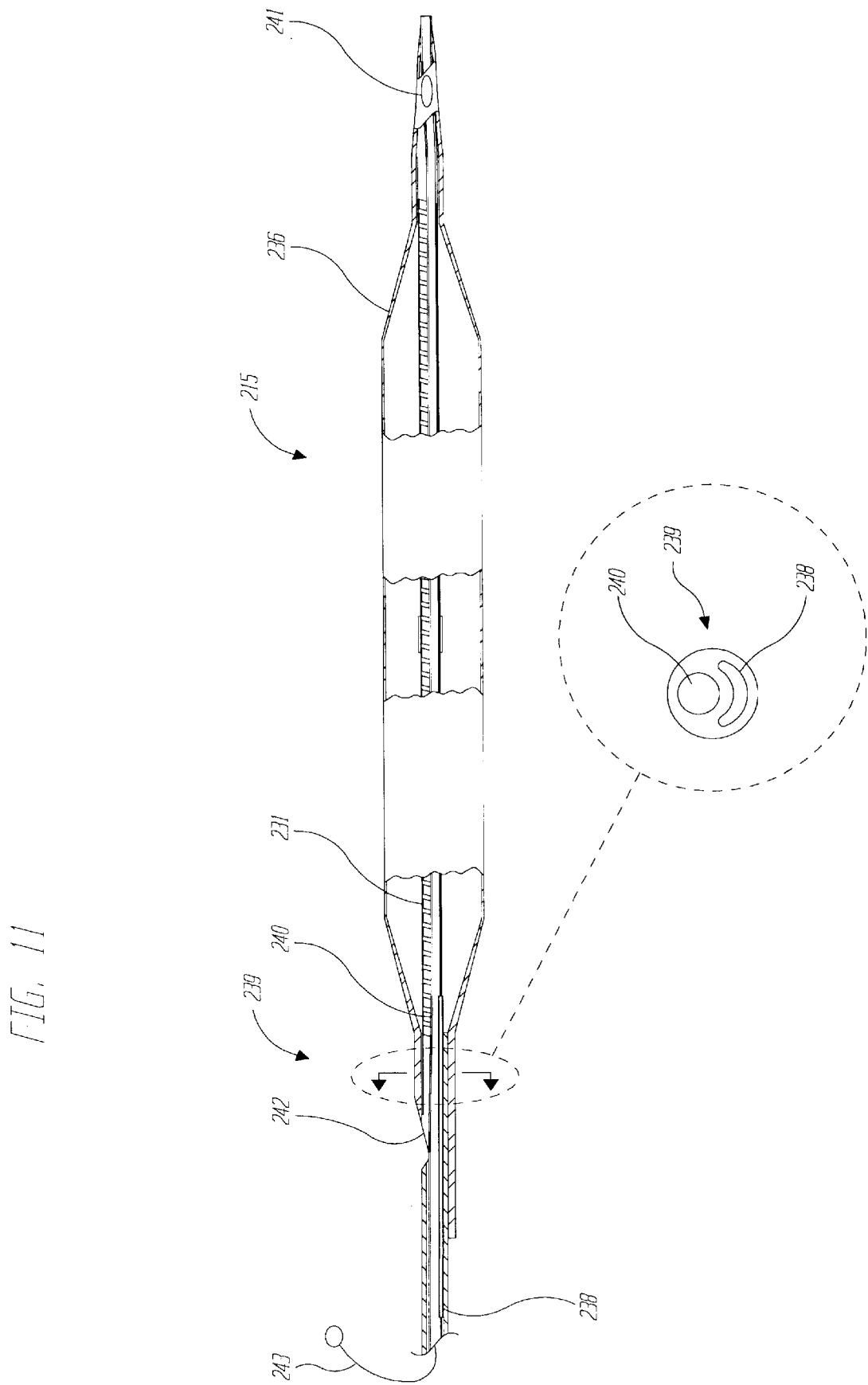

FIG. 11 shows an intravascular flow measurement device 210 incorporated into a perfusion catheter 215. This particular perfusion catheter 215 includes a balloon 236. The perfusion catheter body 239 is generally circular in cross-section with several lumens. The balloon 236 can be inflated by injecting fluid into an inflation lumen 238. After inflation, the patient's blood vessel is perfused by the blood flowing through the main lumen 240 of the perfusion catheter 215. Blood enters the main lumen 240 through an inlet aperture 242 and then exits through apertures in the distal tip 241 of the perfusion catheter 215. A sensor coil 231 is located on the interior wall of the main lumen 240. Consequently, the blood flowing through the main lumen 240 contacts the sensor coil 231 and can be measured with the sensor coil 231. Sensor coil 231 is electrically connected to the calibration and display system 217 through a suitable set of wires shown as cable 243. To calibrate this sensor coil 231, the perfusion catheter 215 is introduced through a sheath or the like and the static temperature and the quiescent current $I_0$ measurements are made before the balloon 236 is deployed and inflated. Since the diameter of the central lumen 240 is known, the blood flow velocity measurement can be used to measure the mass flow rate of blood in the artery which may prove desirable in many clinical settings.

It is also contemplated that the flow sensor may be incorporated into a tube mounted on the end of a mandrel. The tube would have a short length to allow for rapid exchange and would have an inside diameter sufficiently large to pass over a guide wire or another intravascular device. The mandrel would be sufficiently long to manipulate the tube in-vivo while the mandrel remains in-vitro.

In either form of intravascular flow velocity measurement device, the dynamic measurements are made by heating the sensor coil above the ambient blood temperature and monitoring the current draw of the sensor coil 230. Suitable computation and control measurements are made and the resulting instantaneous flow velocity is available as a numeric value on a suitable data display 218 or available through an output terminal 219 to a suitable real time analog display (not shown).

Figure 12:
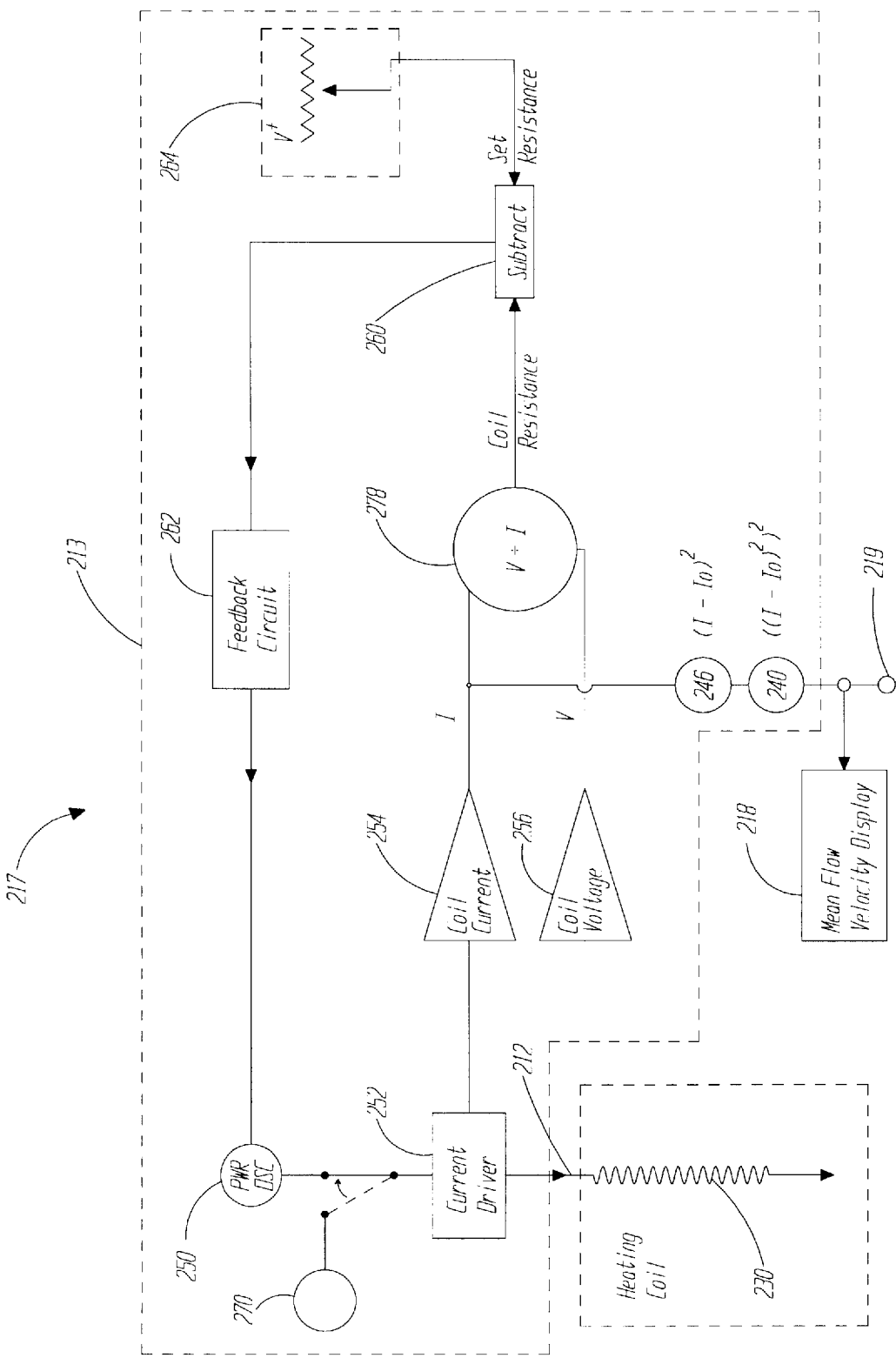

FIG. 12 shows an illustrative circuit for carrying out a flow velocity measurement with the intravascular flow velocity measurement device 210 shown in either FIG. 10 or FIG. 11. It should be appreciated that the intravascular flow velocity measurement system 216 can be positioned in a number of ways and the exemplary system described herein can be modified in various ways without departing from the scope of the invention. One exemplary partitioning of functions would rely on digital devices to perform the calculation function shown in block 246. A brief description of the flow measurement process facilitates an understanding of this block schematic diagram.

In general, the flow velocity measurement is derived from a measurement of the current required to maintain the temperature of the sensor coil above the ambient temperature at the measurement site. Expressed as an equation, the velocity "v" is given by $v=(c(I-I_0)^4)$, where "I" is the measured current required to elevate the temperature of the sensor coil 230 in the presence of blood flow. The value of the quiescent current to maintain the temperature elevation in the no flow condition is represented by "$I_0$".

The conversion constant "c" appears to depend strongly on the physical characteristics of the sensor coil 230 and the related insulating spacer 228 and device structure. Conventional manufacturing techniques are sufficient to produce intravascular measurement devices 210 with similar values of the constant "c". It is not expected that the calibration and display system 217 will have to accommodate devices with widely varying values of "c". The constant "c" also varies with the thermal properties of the fluid. Testing has shown that "c" does not vary appreciably with hematocrit in mammalian blood.

The set of calibration measurements includes measurement of ambient temperature at or near the flow measurement site in still blood at a so-called calibration site. In the present system, the sensor coil 230 is interrogated with a small current to determine the resistance of the sensor coil. The sensor coil is coupled to the calibration and display system via sensor coil leads 221 and 223 which have a characteristic resistance. In general, it is desirable to minimize the lead resistance. The preferred sensor coil material is selected based upon the lead resistance with silver, platinum and nickel iron alloy being useful, depending on the lead resistance. Each of these sensor coil materials exhibits a resistance that is a linear function of temperature. The current level and duration of the interrogation pulses does not materially raise the temperature of the sensor coil. This measurement may be made with an AC current or a DC current.

The measured blood temperature is used as a base for temperature difference set point. The preferred temperature difference is 5 degrees or less. This temperature differential can be adjusted by the physician if desired. A feedback system drives the sensor coil to the desired temperature and maintains it at that temperature. Although both linear and non-linear feedback can be used, the preferred feedback scheme is non-linear. It is desirable to rapidly approach the set point temperature to maintain high dynamic range but it is also important not to overshoot the target temperature and potentially injure the blood. It is undesirable to overheat the sensor coil 230 in the vessel and yet flow-induced cooling must be quickly overcome to make pulsatile measurements.

Turning to the schematic diagram of FIG. 12, an exemplary calibration and display system 217 is shown in block form. In the measurement mode, the oscillator 250 generates pulses which are used by current driver 252 to drive current through the sensor coil 230 or sensor coil 231. The current through the sensor coil and the voltage across the sensor coil are available in analog form through operational amplifiers 244 and 246. A divider 248 forms the quotient of the two values generating a coil resistance measurement. The subtractor circuits 260 and feedback circuit 262 together alter the pulse width and duty cycle of the oscillator 250. Thus, in operation, the duty cycle of the oscillator 250 reflects the current draw of the coil required to maintain the constant temperature differential. The instantaneous current through the sensor coil 230 is related to the flow velocity. In practice, the displayed flow value at data display 218 is instantaneous coil current "I" raised to the fourth power as represented by blocks 246 and 247. This value is proportional to the flow velocity and it is delivered to the output terminal 219. This sharp dependence of flow measurement on measured current makes the in situ calibration important, especially for quantitative measurements.

In the calibration mode, the sensor coil is withdrawn into a sheath to the calibration position for a static blood temperature measurement. Switch 268 is used to couple the low current source 270 through the sensor coil 230. This current driver is set to deliver low current pulses to interrogate the sensor coil to determine body temperature at the calibration site. Although switch 268 may be used to select a separate low duty cycle current source 270 to generate the required interrogation current, other current sources may be substituted. The coil resistant measurement during the calibration process is monitored and used to set the value of resistor divider 264. This potentiometer sets the target temperature of the dynamic measurement. During the dynamic measurement mode, the current driver 252 is enabled to produce higher current pulses to drive the coil 230 to a higher set point temperature.

Having thus described the intravascular flow measurement system 216 and the method for using it, it should be apparent that many changes can be made to the system without departing from the scope of the invention.

Combined Pressure and Flow Measurement Embodiment

Figure 13:
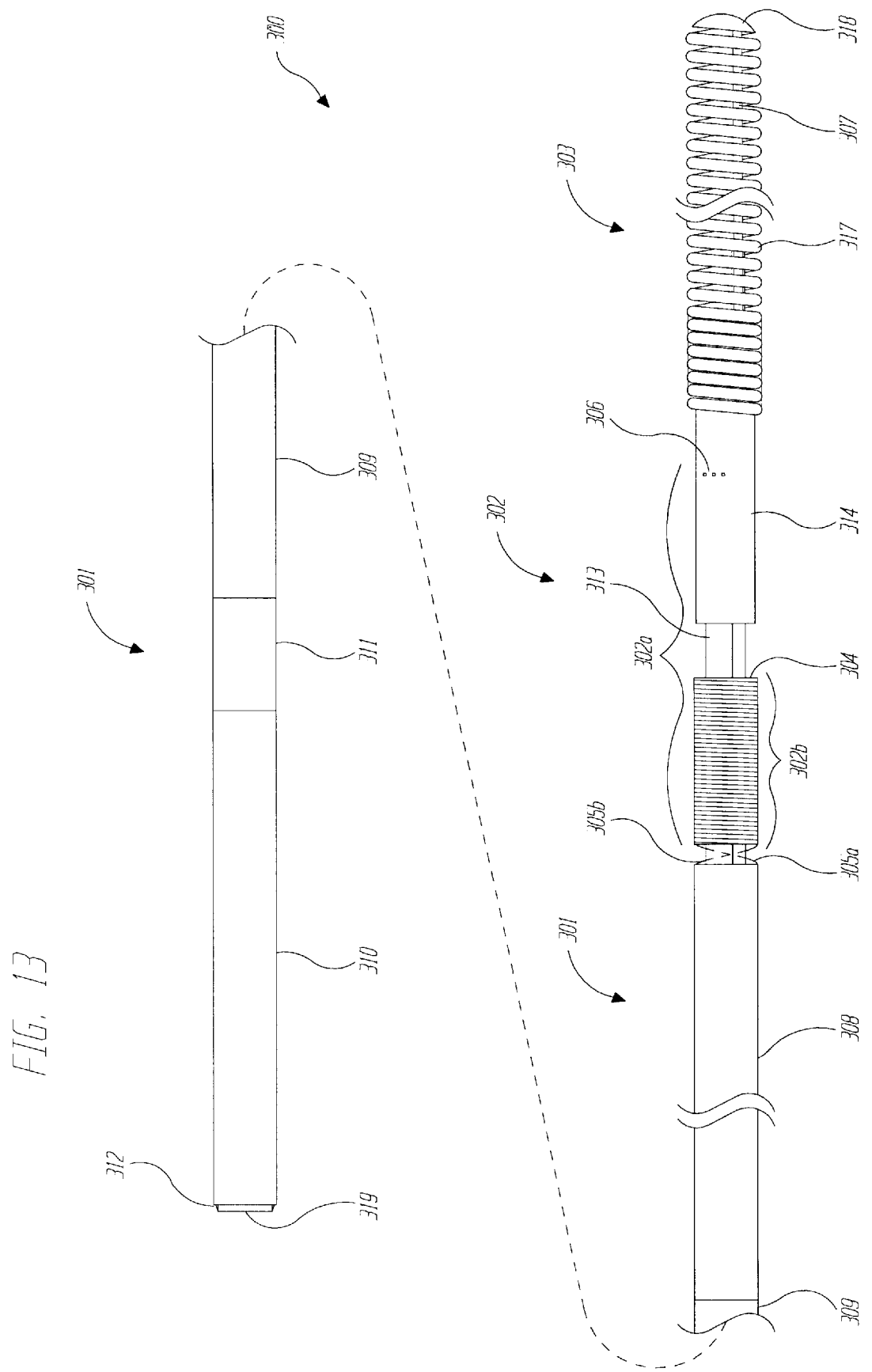
FIGS. 13–18 illustrate a combined pressure and flow measurement system of the present invention.

Refer now to FIGS. 13–18 which illustrate a combined pressure and flow measurement system of the present invention. With reference to FIG. 13, a combined pressure and flow measurement system is shown in the form of a guide wire 300. Those skilled in the art will recognize that the combined pressure and flow measurement system may be incorporated into other intravascular devices such as a balloon dilation catheter, a guide catheter or an introducer sheath. The combined pressure and flow measurement guide wire 300 includes a shaft 301 with a transducer 302 connected adjacent its distal end. A spring tip 303 is connected to the distal extremity of the shaft 301 and facilitates atraumatic navigation of the guide wire 300 through the vascular system.

The transducer 302 includes a sensor coil 304 having leads 305A and 305B. Coil lead 305B is connected to main hypotube 309 by means which will be described in more detail with reference to FIGS. 13 and 14. Coil lead 305A is electrically connected to proximal hypotube 310 via core wire 319 which is soldered to the proximal hypotube 310 at solder joint 312. Main hypotube 309 is electrically insulated from proximal hypotube 310 by a tubular spacer 311. The proximal portion of the main hypotube 309 and the proximal hypotube 310 serve as electrical contacts to a connector (not shown).

The transducer assembly 302 includes sensor coil 304 which surrounds sensor tube 313 which in turn contains a column of ferrofluid substantially as described with reference to FIGS. 7–8. "The transducer 302 includes a pressure transducer portion 302a and a flow transducer portion 302b, each of which may include common components as described herein. " Spring tip connector tube 314 facilitates connection of the transducer assembly 302 to the spring tip assembly 303. Spring tip connector tube 314 also includes a series of pressure inlet holes 306 which provide for fluid communication between the interior of the sensor tube 313 and the vascular lumen.

The proximal end of the spring tip coil 317 is connected to the distal end of the spring tip connector tube 314. The distal end of the spring tip coil 317 is connected to the distal end of the safety wire 307 to form a atraumatic tip 318.

Figure 14:
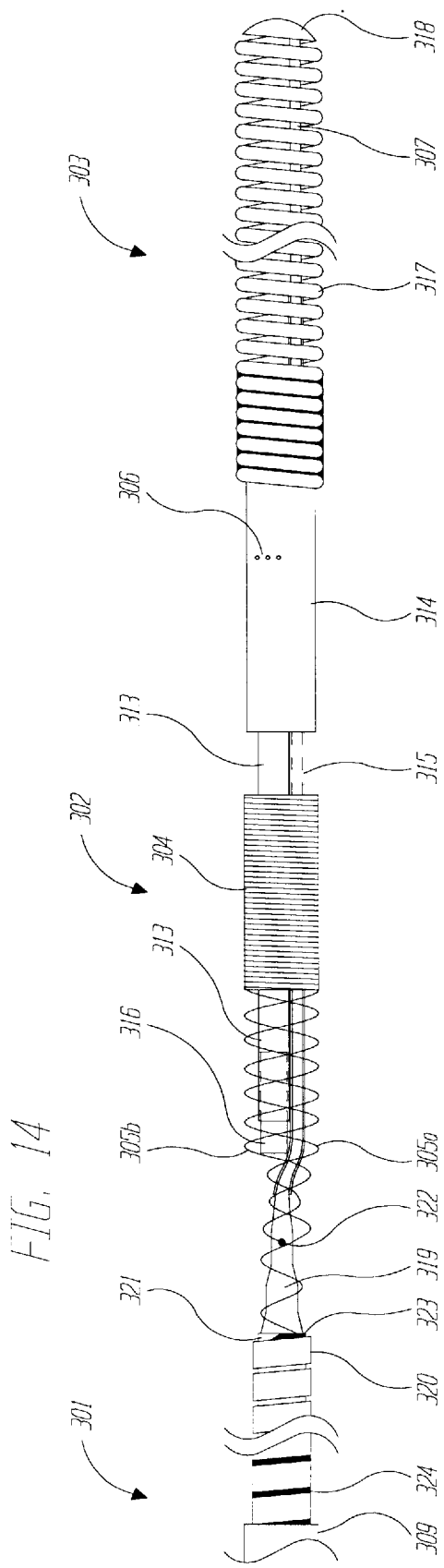
Figure 15:
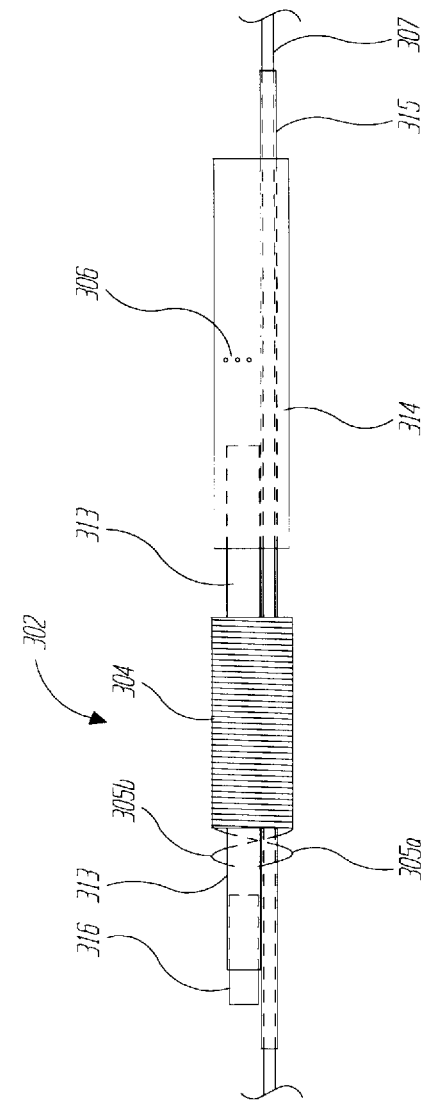

Refer now to FIGS. 14 and 15 which show in greater detail the distal assembly of the combined pressure and flow measurement guide wire 300. In particular, FIG. 14 shows the distal assembly with cover tube 308 removed. FIG. 15 shows the distal subassembly of the transducer 302.

Referring to FIG. 15, coil 304 is wound around sensor tube 313 and safety wire insulator 315. Sensor tube 313 contains a column of ferrofluid (not shown) which is longitudinally moveable therein. The proximal end of the sensor tube 313 is plugged with sensor tube seal 316. Blood pressure within the vascular lumen communicates with the interior of the sensor tube 313 by way of pressure inlet holes 306 in spring tip connector tube 314. Spring tip connector tube 314 is sealingly secured to sensor tube 313 and safety wire insulator 315.

Referring now to FIG. 14, sensor coil 305 includes leads 305A and 305B. Lead 305A is electrically connected to the core wire 319 at solder joint 322. Coil lead 305B is electrically connected to a ribbon lead 320 at solder joint 323. The core wire 319 is electrically insulated from the ribbon lead 320 by insulator layer 321. The ribbon lead 320 is electrically connected to the main hypotube 309 at solder joint 324. Core wire 319 extends proximally and is electrically connected to proximal hypotube 310 at solder joint 312 (as best seen in FIG. 13).

Coil 304 may be made from No. 50 AWG silver/ML wire with two layers of 250 turns each. Sensor tube 313 may be made of metalized polyimide with an inside diameter of approximately 0.005 inches and an outside diameter of about 0.0065 inches. The sensor tube 313 may be metalized with a thin film of gold, silver, aluminum, or other metal to prevent air permeation through the polyimide. Sensor tube 313 may have a length of approximately 0.60 inches with the sensor coil 304 positioned approximately in the middle of the sensor tube 313. Sensor tube seal 316 may be made of a non-magnetic material such as a Nitinol with a length of approximately 0.10 inches and an outside diameter sufficient to securely connect and seal to the proximal end of the sensor tube 313.

Safety wire insulator 315 may be made of polyimide with an inside diameter of approximately 0.0025 inches and an outside diameter of approximately 0.0031 inches. The safety wire insulator 315 may have a length of approximately 1.0 inches.

Spring tip connector tube 314 may be made of polyimide with an inside diameter of approximately 0.010 inches and outside diameter of approximately 0.12 inches. Spring tip connector tube 314 may have a length of approximately inches with a series of pressure inlet holes 306 drilled through the wall of the tube. Approximately 3 to 10 pressure inlet holes 306 may be utilized with a diameter ranging from 0.004 to 0.008 inches.

All non-electrical connections involving polymer tubes may be made using a suitable medical grade adhesive such as cyanoacrylate.

The distal end of the safety ribbon 307 may be soldered or welded to the distal end of the spring tip coil 317 to form an atraumatic tip 318. Spring tip 303 may have a length of about 1.0 inches with an outside diameter of approximately 0.014 inches. Spring tip coil 317 may be made of any suitable radiopaque metal such as a platinum-iridium alloy. The proximal end of the spring tip 303 may be adhesively secured to the spring tip connector tube 314 by a suitable medical grade adhesive. Core wire 319 may be made of stainless steel with diameters ranging from about 0.008 inches proximally to about 0.005 inches distally where the core wire 319 is formed into a safety wire 307 with a diameter of 0.002 inches.

Sensor 302 is preferably coated with a hydrophilic copolymer (HPC) to prevent the coagulation and accumulation of blood thereon. The remainder of the guide wire 300 may be coated with a lubricious material such as HPC or TEFLON to reduce friction and enhance intravascular manipulation.

All electrical connections may be made using a suitable soldering material such as a tin-lead or silver solder. Ribbon lead 320 is preferably made of silver with a width of about 0.003 to 0.006 inches and a thickness of about 0.001 inches. Hypotube 309 may be made of 440 stainless steel with a length of approximately 5 feet and outside diameter of approximately 0.014 inches and an inside diameter of approximately 0.011 inches.

Insulating layer 321 may be made of a suitable material such as polyimide with an inside diameter conforming to the outside diameter of the core wire 319 and a wall thickness of about 0.0005 inches. Core wire 319 and insulating layer 321 extend proximally through hypotube 309, insulating spacer 311 and proximal hypotube 310 where the core wire 319 is soldered to the proximal hypotube 310 by solder joint 312. Proximal hypotube 310 may have a length of approximately 0.65 inches with the same outside diameter and inside diameter as hypotube 309. Insulator 311 may be made of polyimide with an outside diameter of 0.014 inches, an inner diameter of about 0.010 inches, and a length of about 0.05 inches. Cover tube 308 may be made of polyimide with an inside diameter of about 0.012 inches, an outside diameter of 0.014 inches, and a length of approximately 10 to 15 inches.

The overall diameter of the combined pressure and flow measurement guide wire 300 is approximately 0.014 inches to correspond to the diameter of conventional coronary guide wires.

The combined pressure and flow measurement guide wire 300 may be used in substantially the same way as the pressure measurement system (FIGS. 1–8) and the flow measurement system (FIGS. 9–12) with the following modifications. Recall that the blood pressure and blood flow velocity may be calculated from the inductance and resistance of the coil 304. Pressure is linearly proportional to inductance (L) and flow velocity is linearly proportional to $(I-I_0)^4$ where I is equal to the current required to maintain the resistance (R) of the coil 304 constant and $I_0$ is equal to the calibration current required to maintain the resistance of the coil 304 at zero flow. In order to measure blood pressure and blood flow simultaneously, it is necessary to separate the resistance (R) and inductance (L) of the coil 304. Several methods may be employed to electrically separate the resistance and inductance characteristics of the coil 304.

Figure 16:
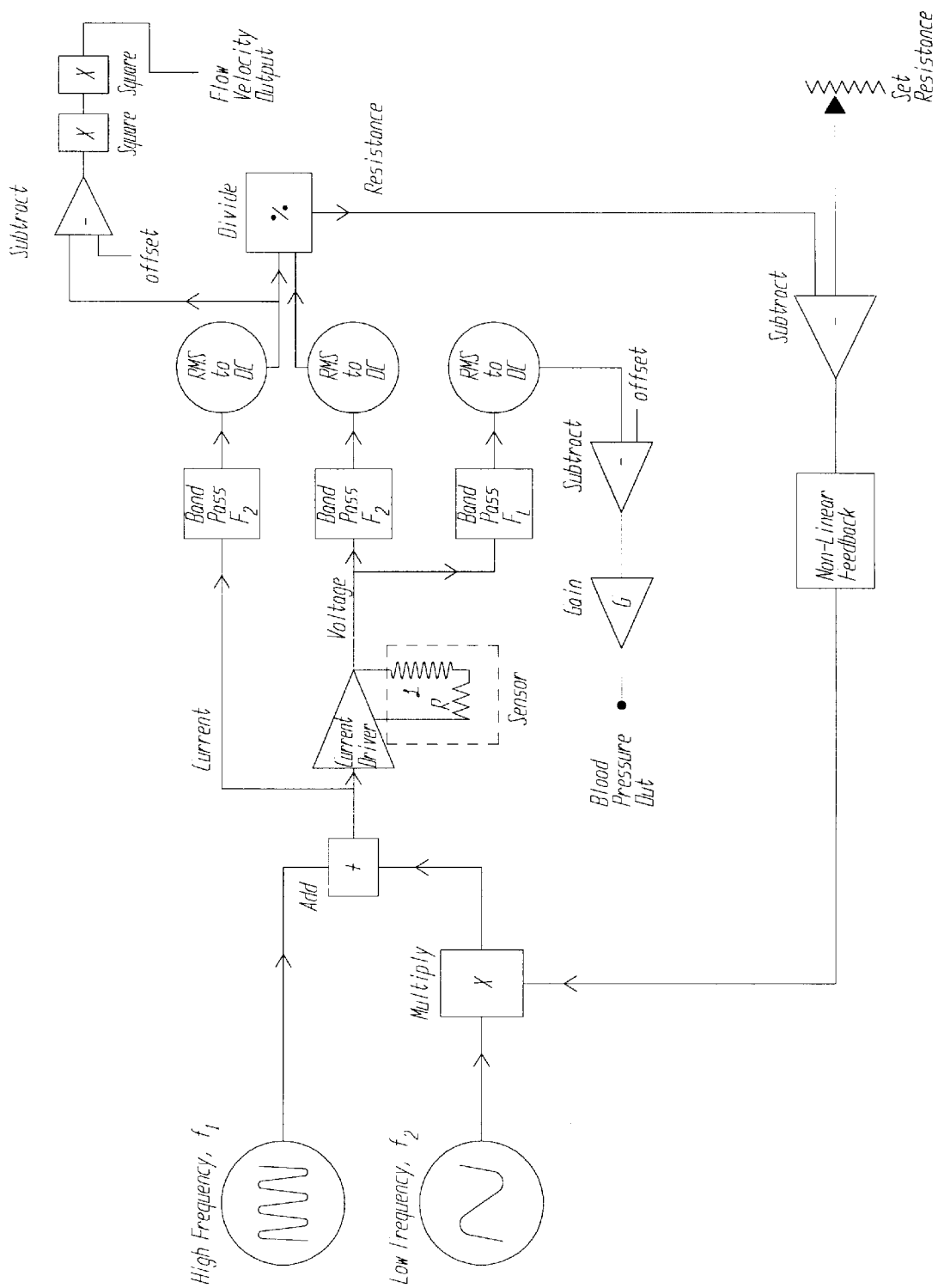

A first method utilizes a frequency separation circuit as illustrated by the block diagram in FIG. 16. The frequency separation method takes advantage of the impedance equation $Z=\sqrt{R^2+\omega^2 L^2}$ where Z=impedance, R=resistance, $\omega$=frequency$\times 2\pi$, and L=inductance. Accordingly, R may be measured at a low frequency with minimal distortion from the reactance component ($\omega L$). In a similar manner, the inductance (L) may be measured at a high frequency with little or no distortion from the resistance component (R). Having simultaneously determined the resistance and inductance of the coil 304, the blood pressure and flow velocity may be calculated where pressure is linearly proportional to inductance (L) and flow velocity is linearly proportional to $(I-I_0)^4$.

Figure 17:
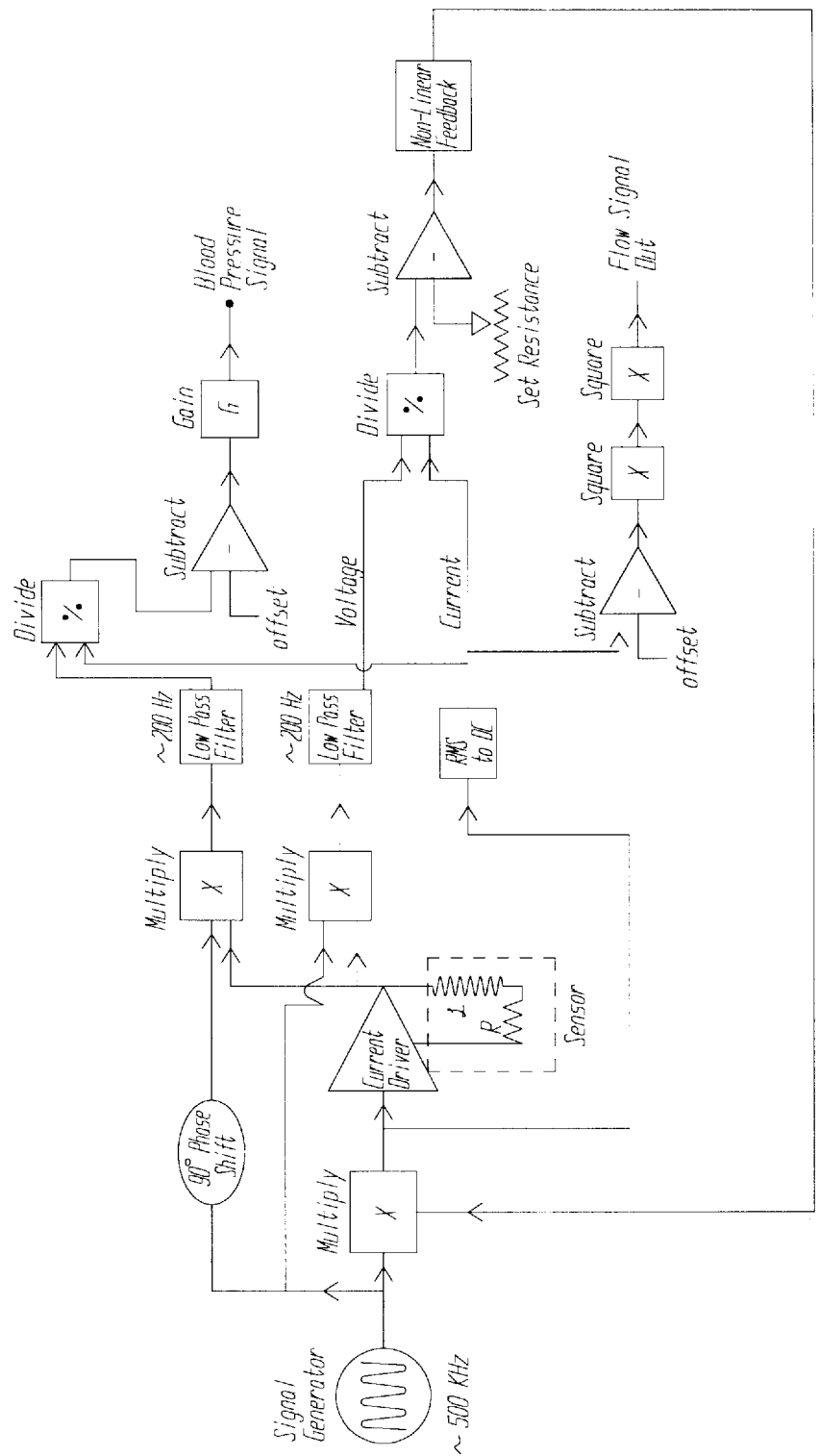

Another method of separating the resistance and inductance characteristics of the coil 304 is to utilize quadrature separation circuitry as illustrated by the block diagram in FIG. 17. The sensor complex impedance is given by $R+i\omega L$ showing that the resistance and inductive reactance are 90 degrees out of phase. Basically, the resistance R is measured at a frequency which is 90 degrees out of phase with the frequency at which the inductance is measured. This is accomplished by mixing the sensor voltage with reference signals which are in phase and 90 degrees out of phase with the drive signal. As described previously, blood pressure and blood flow velocity may then be calculated.

Figure 18:
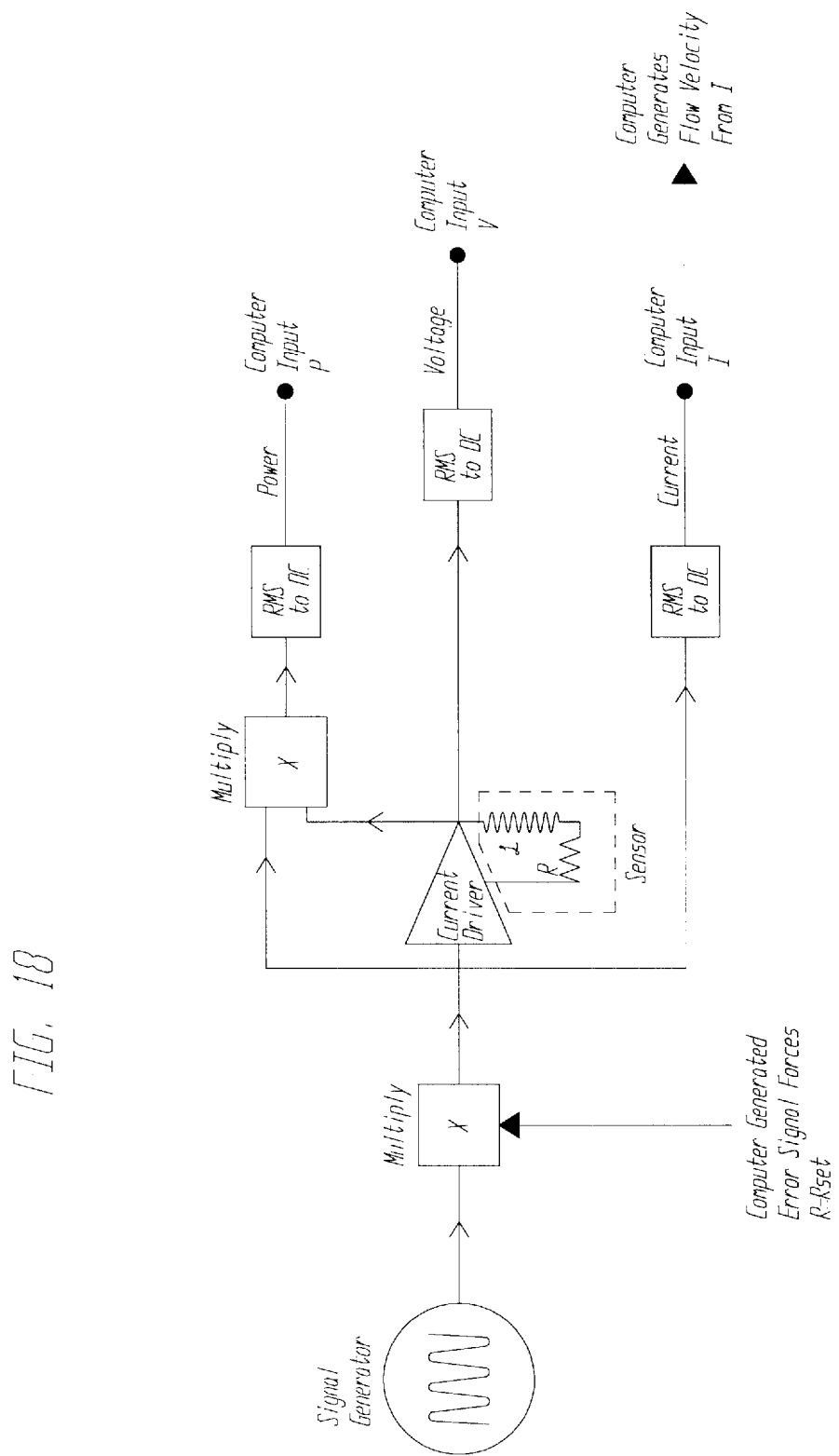

Yet another method is to utilize computational separation circuitry as illustrated by the block diagram in FIG. 18. The computational separation circuitry calculates the pressure (P) recognizing that $P \propto \omega L = \sqrt{(V/I)^2-(P/I^2)^2}$, where V, I and P are defined in FIG. 18. The computational separation circuitry calculates the flow velocity (v) recognizing that $v \propto (I-I_0)^4$. Accordingly, the pressure and flow velocity may be determined by computing the results of these equations.

Simultaneous measurements may also be made utilizing a commercially available component tester such as Model No. 878 Universal LCR Meter available from BK Precision. However, this instrument operates at a lower frequency than the preferred frequency of the present invention (500 KHz).

It may be desirable to determine average or peak flow through a given artery or arterial system rather than a specific point within an artery. One method of accomplishing this is to utilize a flow centering element such as a spherical ball or spherical surface located distal of the sensor 302. The flow centering element will cause the sensor 302 to be positioned in the highest velocity flow point. The highest velocity for laminar flow in a circular lumen is in the center of the lumen. Flow velocity measurements may be made at this point and the average flow, peak flow and flow rate may be determined using standard laminar pipe flow equations.

Another method of determining generalized flow parameters as opposed to site specific flow parameters is to calculate coronary flow reserve (CFR). CFR is the ratio of peak to resting coronary blood flow (dimensionless number) and is perceived by some to be a good measure of stenosis significance. Peak flow is measured after an injection of a pharmacological agent (e.g., papaverine) to relax smooth muscle cells (i.e. vessel wall) and resting blood flow is measured immediately before the injection. Accordingly, CFR may be measured independent of the precise position of the sensor 302 as long as the position remains the same during each flow measurement.

It is also contemplated that the sensor 302 may be used to measure radial flow which tends to indicate the existence of turbulent flow. Turbulent flow has been associated with intralumenal restrictions caused by such things as a stenosis or a poorly deployed intravascular stent. Radial flow may be measured by utilizing a sensor shield (not shown) which restricts axial flow across the sensor 302 but permits radial flow across the sensor. The sensor shield may, for example, be in the form of a tube surrounding the sensor wherein the tube has a plurality of oppositely-facing holes about the circumference of the tube. By way of example, three bands of four (4) holes each with a diameter of about 0.008 inches are drilled in the wall of the tubular shield. The bands may be spaced 0.10 inches apart and the tubular shield may be made of polyimide with an inside diameter of about 0.032 inches, an outside diameter of about 0.034 inches and a length of about 0.95 inches. The shield tube is placed around the sensor coil 302 with the ends of the shield tube sealed on either side of the sensor 302 to eliminate axial or longitudinal flow. It should be noted that the sensor shield tube may also seal the sensor 302 from axial or longitudinal flow by other means not specifically mentioned herein.

It is also contemplated that the sensor shield may have holes around only a portion of the circumference of the tube. Having holes on only one side of the tube would provide a means to detect rotational flow while eliminating longitudinal and transverse flow. It is further contemplated that a multiplicity of hole patterns may be configured for a variety of flow measurements. For example, holes may be arranged to measure radial or transverse flow in a first direction and radial or transverse flow in a second direction which is orthogonal to the first direction. The sensor shield may also be movable such that axial flow may be measured when the shield is retracted and radial or transverse flow may be measured when the shield is positioned over the sensor. Accordingly, an entire three-dimensional flow pattern may be measured.

The sensor shield concept may also be utilized with other transducers to measure radial flow. For example, the sensor shield may be adapted for use with an acoustic sensor as described in commonly-assigned U.S. patent application entitled VIBRATION SENSING GUIDE WIRE Ser. No. 08/278,552, which is specifically incorporated herein by reference. In addition, the sensor shield may be incorporated into the alternative flow measurement embodiment described below.

Alternative Flow Measurement Embodiment

Figure 19:
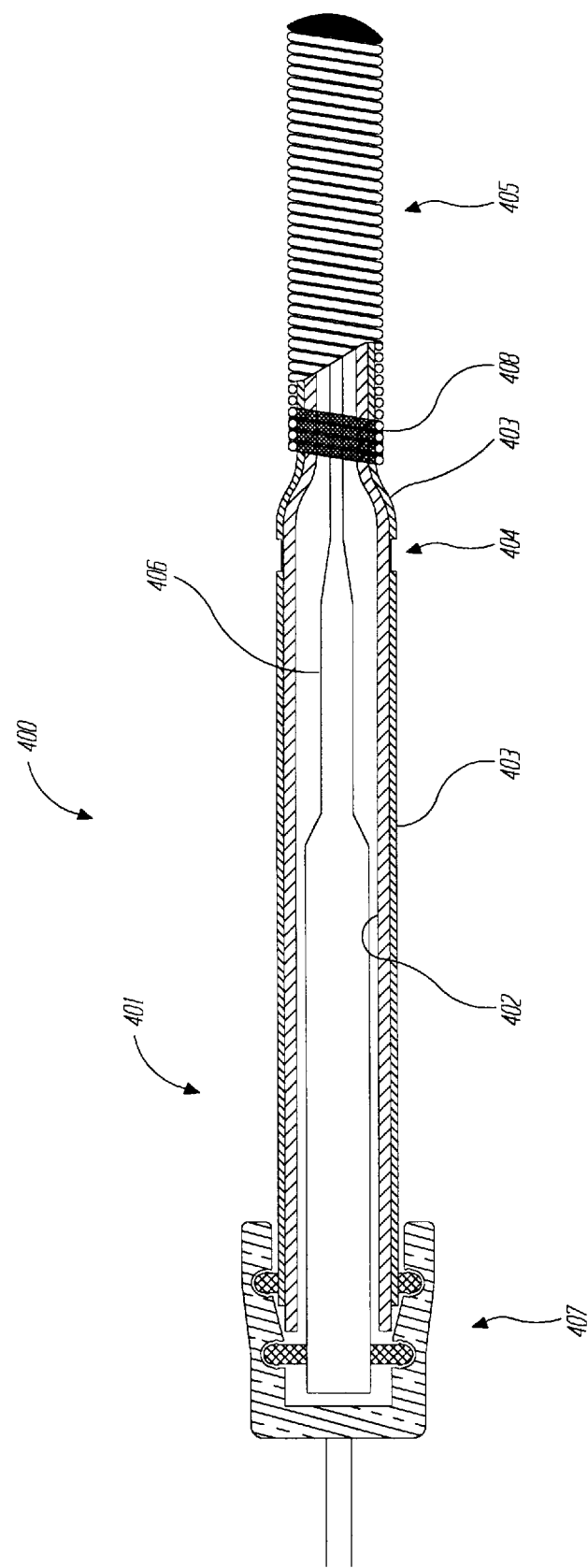
FIG. 19 illustrates an alternative blood flow measurement system.

Refer now to FIG. 19 which shows an alternative flow measurement embodiment in the form of a guide wire 400. This embodiment may also be adapted for use on a catheter such as a perfusion balloon catheter. The flow measurement guide wire 400 may be used in substantially the same way as the flow measurement system described with reference to FIGS. 9–12 while making the necessary accommodations for the different anemometer structure.

The flow measurement guide wire 400 includes an elongate shaft 401 comprising a tube 402 having a core wire 406 extending therethrough. The tube 402 has a metal film coating on its exterior surface extending from the proximal end of the tube 402 to the distal end of the tube 402. The metal film coating 403 includes an interruption or gap 404 adjacent the distal end of the tube 402. The interruption 404 comprises a narrow region where the coating thickness is reduced such that the electrical resistance per unit length across the interruption 404 is greater than the resistance per unit length of the remainder of the metal coating 403. The metal film coating 403 may be electroplated, evaporated, sputtered, or a combination thereof onto tube 402.

A spring tip 405 has a proximal end connected to the distal end of the tube 402 and electrically connected to the metal film 403 distal of the interruption 404. The distal end of the spring tip 405 is connected to the distal end of the core wire 406. A continuous electrical path is defined from the proximal end of the metal film 403 across the interruption 404 continuing through the solder 408 to the core wire 406 and continuing to the proximal end of the core wire 406.

At the proximal end of the shaft 401, an electrical connector 407 is mounted on the shaft such that one lead is connected to the core wire 406 and the other lead is connected to the metal film 403. Electrical connector 407 is wired to the processing circuitry (FIGS. 16, 17, 18) and may include a rotational junction to allow the guide wire 400 to be rotated independently of the proccessing circuitry.

The interruption 404 substitutes the coil anemometer described with reference to FIGS. 9–12. By way of example, not limitation, the metal film 403 may comprise a thin coating on a polyimide tube 402. The metal film may be selected from a wide range of conductive metals such as aluminum, gold, silver or another metal with a sufficiently large termperature coefficient to produce an electrical response to flow. The metal film may have a thickness of approximately 10,000 to 400,000 Å and the interruption may have a film thickness of approximately 100 to 500 Å. Given a metal film 403 thickness of about 20,000 Å and an interruption 404 thickness of about 100 Å, the metal film 403 has a resistance per unit length of approximately 0.667Ω per inch and the interruption 404 has a resistance per unit length of approximately 250 to 1,000Ω per inch, depending on the thickness tolerance. The slot width may, for example, be between 0.02 inches and 0.50 inches (±10%).

It is contemplated that the tube 402 may have a gold metal film with a thickness on the order of 100,000 to 400,000 Å to enhance its radiopaque properties. With such a metal film, the distal portion of the shaft 401 would appear under fluoroscopy as a dark line (also referred to as a "ghost image") to assist the treating physician navigate the vasculature and perform the desired medical procedure. The film thickness may vary along the length of the tube 402 to provide areas of varying radiopacity. Other suitable radiopaque materials may be employed.

It is also contemplated that the sensor shield described previously may be employed to measure discrete components of the blood flow pattern. It is further contemplated that a series of sensor regions (i.e., interruptions 404) may be used to determine flow patterns along the length of the vascular lumen. The sensor regions may also utilize sensor shields as described previously. The signal from each of the sensor regions would be separated using phasic signal separation. Knowing the distance (d) between the sensor regions and the time (Δt) required for a flow pattern to pass from one sensor region to another sensor region, an average flow velocity may be calculated by d÷Δt. Thus a continuous, in-vivo calibration of mean flow velocity is obtained and may be used to accurately scale the velocity waveform.

The metal film 403 may extend around the entire circumference of the tube 402. Alternatively, the metal film 403 may extend around only a portion of the outer circumference of tube 402. In addition, the interruption or gap 404 may extend around either the entire circumference of the tube or a portion thereof. Having the metal film 403 cover only a portion of the circumference of the tube 402 allows the interruption 404 to be rotated into the main flow when the guide wire is pushed against the interior wall of the vessel.

The tube 402 may be made of polyimide with a length of about 60 inches, an outside diameter of about 0.008 to 0.018 inches and a wall thickness of about 0.0005 to 0.002 inches. The core wire 406 may be made of 304v stainless steel with a length of about 60 inches and a proximal diameter of about 0.006 to 0.015 inches tapering to about 0.002 to 0.005 inches distally. The distal extremity of the core wire 406 may be stamped into the shape of a ribbon to provide additional flexibility and shapability. The spring tip may be made of conventional materials. Electrical connections may be made by soldering or welding and other connections may be formed utilizing a medical grade adhesive.

The shaft 401 may include a hypotube proximal section and a polymer tube distal section. This would provide additional pushability for advancing the catheter into the vasculature. In addition, this would reduce the area of metal film exposed to damaging abrasion. The hypotube must be insulated from the corewire 406 and electrically connected to the metal film 403.

While this invention has been shown and described in connection with the preferred embodiments, it is apparent that certain changes and modifications, in addition to those mentioned above, may be made from the basic features of the present invention. Accordingly, it is the intention of the Applicant to protect all variations and modifications within the true spirit and valid scope of the present invention.

What is claimed is:

1. An intravascular device for measuring blood pressure and flow, comprising:
   a. an elongate shaft having a proximal end and a distal end, the distal end of the elongate shaft adapted to be inserted into the vasculature of a patient;
   b. a pressure transducer connected to the distal end of the elongate shaft, wherein the pressure transducer includes a column of ferrofluid which moves in response to changes in intravascular blood pressure; and
   c. a flow transducer connected to the distal end of the elongate shaft, the flow transducer sharing at least two electrically conductive leads with the pressure transducer.

2. An intravascular device for measuring blood pressure and flow as in claim 1, wherein the pressure transducer includes an electrically conductive coil surrounding the ferrofluid.

3. An intravascular device for measuring blood pressure and flow as in claim 2, wherein the coil is electrically coupled to an external measurement circuit.

4. An intravascular device for measuring blood pressure and flow as in claim 3, wherein the measurement circuit measures inductance of the coil as the ferrofluid moves in response to changes in intravascular blood pressure.

5. An intravascular device for measuring blood pressure and flow as in claim 4, wherein the coil is supplied with an electrical current to heat the coil to a temperature above body temperature.

6. An intravascular device for measuring blood pressure and flow as in claim 5, wherein the measurement circuit measures resistance of the coil as the resistance of the coil changes in response to intravascular blood flow.

7. An intravascular device for measuring blood pressure and flow as in claim 6, wherein the measurement circuit measures resistance and inductance simultaneously.

8. An intravascular device for measuring blood pressure and flow as in claim 7 wherein the measurement circuit utilizes frequency separation to measure resistance and inductance simultaneously.

9. An intravascular device for measuring blood pressure and flow as in claim 7 wherein the measurement circuit utilizes phasic separation to measure resistance and inductance simultaneously.

10. An intravascular device for measuring blood pressure and flow as in claim 7 wherein the measurement circuit utilizes computational analysis to measure resistance and inductance simultaneously.

11. An intravascular device for measuring blood pressure and flow, comprising:
    a. an elongate shaft having a proximal end and a distal end, the distal end of the elongate shaft adapted to be inserted into the vasculature of a patient;
    b. a pressure transducer connected to the distal end of the elongate shaft; and
    c. a flow transducer connected to the distal end of the elongate shaft, the flow transducer sharing at least two electrically conductive leads with the pressure transducer, wherein the pressure transducer and the flow transducer share an electrically conductive coil surrounding a chamber containing a ferrofluid, the coil having electrical characteristics which change in response to changes in blood pressure and flow.

12. An intravascular device for measuring blood pressure and flow as in claim 11 wherein the electrical characteristics include resistance and inductance, the resistance of the coil changing in proportion to blood flow and the inductance of the coil changing in proportion to blood pressure.

13. An intravascular device for measuring blood pressure and flow as in claim 12 wherein the coil is electrically connected to a measurement circuit which electrically separates the electrical characteristics of the coil.

14. An intravascular device for measuring blood pressure and flow as in claim 13 wherein the measurement circuit electrically separates the resistance and the inductance of the coil.

15. An intravascular device for measuring blood pressure and flow as in claim 11 wherein the electrical characteristics include inductance and current draw required to maintain constant resistance, the inductance of the coil changing in proportion to blood pressure and the current draw of the coil changing in relation to blood flow.

16. An intravascular device for measuring blood pressure and flow as in claim 15 wherein the coil is electrically connected to a measurement circuit which electrically separates the electrical characteristics of the coil.

17. An intravascular device for measuring blood pressure and flow as in claim 16 wherein the measurement circuit electrically separates the current draw and the inductance of the coil.

18. An intravascular device for measuring blood pressure and flow, comprising:
   a. an elongate shaft having a proximal end and a distal end, the distal end of the elongate shaft adapted to be inserted into the vasculature of a patient; and
   b. an electrically conductive coil comprising a pressure transducer and a flow transducer, the electrically conductive coil surrounding a chamber containing a ferrofluid, the coil having electrical characteristics which change in response to changes in blood pressure and flow.

19. An intravascular device for measuring blood pressure and flow as in claim 18 wherein the electrical characteristics include resistance or current draw and inductance, the resistance or current draw of the coil changing in proportion to blood flow and the inductance of the coil changing in proportion to blood pressure.

20. An intravascular device for measuring blood pressure and flow, comprising:
   a. an elongate shaft having a proximal end and a distal end, the distal end of the elongate shaft adapted to be inserted into the vasculature of a patient;
   b. a ferrofluid-type pressure transducer connected to the distal end of the elongate shaft; and
   c. an anemometer-type flow transducer connected to the distal end of the elongate shaft.

21. An intravascular device for measuring blood pressure and flow as in claim 20 wherein the measurement circuit utilizes frequency separation to measure resistance and inductance simultaneously.

22. An intravascular device for measuring blood pressure and flow as in claim 20 wherein the measurement circuit utilizes phasic separation to measure resistance and inductance simultaneously.

23. An intravascular device for measuring blood pressure and flow as in claim 20 wherein the measurement circuit utilizes computational analysis to measure resistance and inductance simultaneously.

24. A medical device for detecting turbulent blood flow, the device comprising:
   a sensor having a proximal end, a distal end and a longitudinal axis; and
   a sensor shield which surrounds the sensor to eliminate blood flow which is essentially parallel to the longitudinal axis of the sensor, while allowing detection of radial blood flow, the sensor shield comprising a tube having radially spaced holes, and the tube having a proximal end sealed to the proximal end of the sensor.

25. A medical device for detecting turbulent blood flow as in claim 24, wherein the tube has a distal end sealed to the distal end of the sensor.

* * * * *

(12) REEXAMINATION CERTIFICATE (4432nd)
United States Patent
Hastings et al.

(10) Number: US 5,873,835 C1
(45) Certificate Issued: Aug. 28, 2001

(54) INTRAVASCULAR PRESSURE AND FLOW SENSOR

(75) Inventors: Roger N. Hastings, Maple Grove; Paul T. Feld, Buffalo; Daniel M. Lafontaine, Plymouth; Kenneth R. Larson, Maple Grove; Richard R. Prather, Rogers, all of MN (US)

(73) Assignee: Scimed Life Systems, Inc., Maple Grove, MN (US)

Reexamination Request:
No. 90/005,358, May 11, 1999

Reexamination Certificate for:
Patent No.: 5,873,835
Issued: Feb. 23, 1999
Appl. No.: 08/527,815
Filed: Sep. 13, 1995

Related U.S. Application Data

(63) Continuation-in-part of application No. 08/141,134, filed on Oct. 22, 1993, now Pat. No. 5,450,853, and a continuation-in-part of application No. 08/304,565, filed on Sep. 12, 1994, now Pat. No. 5,617,870, which is a continuation-in-part of application No. 08/055,702, filed on Apr. 29, 1993, now Pat. No. 5,346,508.

(51) Int. Cl.[7] .................................................. A61B 5/0215
(52) U.S. Cl. ............................................. 600/488; 600/561
(58) Field of Search ..................................... 600/485–488, 600/504–505, 476–479, 310, 342, 526, 561

(56) References Cited

U.S. PATENT DOCUMENTS

| | | |
|---|---|---|
| 2,769,337 | 11/1956 | Rich . |
| 3,062,202 | 11/1962 | Hyman et al. . |
| 3,349,623 | 10/1967 | Pastan . |
| 3,352,154 | 11/1967 | Djorup . |
| 3,357,260 | 12/1967 | Detalle . |
| 3,438,253 | 4/1969 | Kuether et al. . |
| 3,750,067 | 7/1973 | Fletcher et al. . |
| 3,789,831 | 2/1974 | Kopaniky et al. . |

(List continued on next page.)

FOREIGN PATENT DOCUMENTS

| | | |
|---|---|---|
| 0 548 872 A1 | 6/1993 | (EP) . |
| WO91/03207 | 3/1991 | (WO) . |
| WO92/00710 | 1/1992 | (WO) . |
| WO92/22240 | 12/1992 | (WO) . |

(List continued on next page.)

*Primary Examiner*—Cary O'Connor

(57) ABSTRACT

An intravascular device for measuring blood pressure and flow is disclosed, which includes an elongate shaft having a pressure transducer and a flow transducer connected to its distal end. The pressure transducer may be a ferrofluid-type pressure transducer and the flow transducer may be an anemometer-type flow transducer. Measurement circuitry is also disclosed which provides a means for simultaneous measurement of both blood pressure and blood flow parameters. A sensor shield may be employed to isolate radial blood flow which is indicative of turbulent blood flow. An alternative blood flow measurement device is also disclosed which utilizes a thin metal film anemometer to measure flow in a vascular lumen.

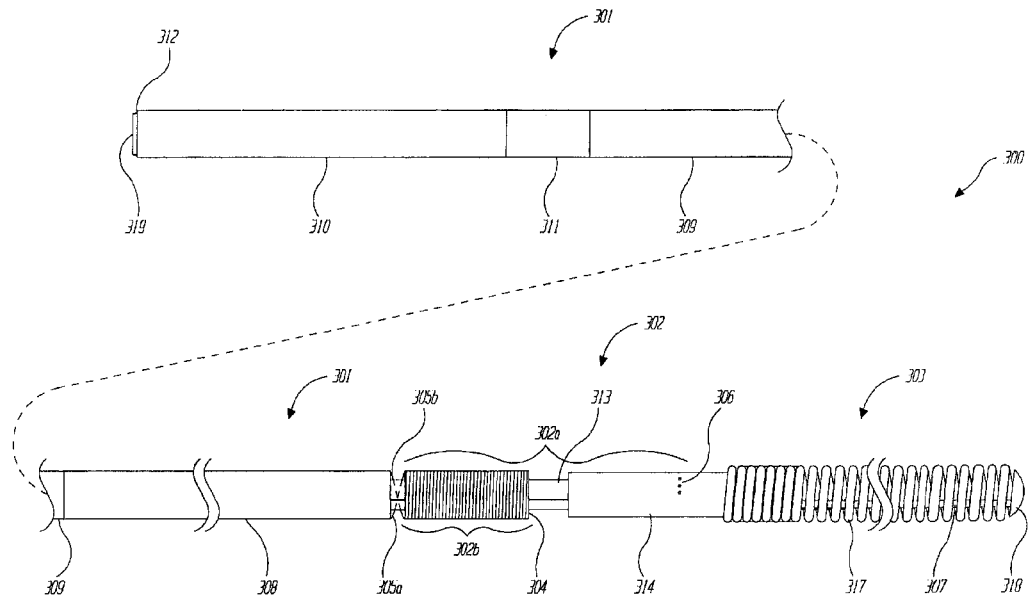

U.S. PATENT DOCUMENTS

| | | |
|---|---|---|
| 3,911,902 | 10/1975 | Delpy . |
| 3,942,382 | 3/1976 | Hök . |
| 4,059,982 | 11/1977 | Bowman . |
| 4,261,208 | 4/1981 | Hök et al. . |
| 4,297,890 | 11/1981 | Hök . |
| 4,413,528 | 11/1983 | Hök et al. . |
| 4,462,259 | 7/1984 | Stoltman et al. . |
| 4,487,206 | 12/1984 | Aagard . |
| 4,691,709 | 9/1987 | Cohen . |
| 4,711,249 | 12/1987 | Brooks . |
| 4,722,218 | 2/1988 | Strader . |
| 4,780,418 | 10/1988 | Kratzer . |
| 4,799,479 | 1/1989 | Spears . |
| 4,809,709 | 3/1989 | Brooks . |
| 4,846,191 | 7/1989 | Brockway et al. . |
| 4,854,326 | 8/1989 | Merrick . |
| 4,874,005 | 10/1989 | Potter . |
| 4,887,610 | 12/1989 | Mittal . |
| 4,920,967 | 5/1990 | Cottonaro et al. . |
| 4,924,872 | 5/1990 | Frank . |
| 4,924,877 | 5/1990 | Brooks . |
| 4,953,553 | 9/1990 | Tremulis . |
| 4,961,433 | 10/1990 | Christian . |
| 4,991,590 | 2/1991 | Shi . |
| 5,002,059 | 3/1991 | Crowley et al. . |
| 5,035,694 | 7/1991 | Kasprzyk et al. . |
| 5,041,089 | 8/1991 | Mueller et al. . |
| 5,050,297 | 9/1991 | Metzger . |
| 5,078,717 | 1/1992 | Parins et al. . |
| 5,094,246 | 3/1992 | Rusz et al. . |
| 5,113,868 | 5/1992 | Wise et al. . |
| 5,114,423 | 5/1992 | Kasprzyk et al. . |
| 5,131,397 | 7/1992 | Crowley . |
| 5,178,153 | 1/1993 | Einzig . |
| 5,178,159 | 1/1993 | Christian . |
| 5,184,621 | 2/1993 | Vogel et al. . |
| 5,190,540 | 3/1993 | Lee . |
| 5,195,375 | 3/1993 | Tenerz et al. . |
| 5,226,423 | 7/1993 | Tenerz et al. . |
| 5,346,508 | 9/1994 | Hastings . |
| 5,450,853 | 9/1995 | Hastings et al. . |

OTHER PUBLICATIONS

"An Ultraminiature Solid–State Pressure Sensor for a Cardiovascular Catheter," H. Chau et al., *IEEE Transactions on Electron Devices*, vol. 35, No. 12, pp. 2355–2362, Dec. 1988.

"Pressure Gradient Analyzer & Guidewire–Mounted Sensor," *Biomedical Technology Information Service*, p. 210, Oct. 15, 1991.

FloWire® /FloMap® Report, 4–pg. brochure from Cardiometrics®, Jan. 1992.

"Validation of a Doppler Guide Wire for Intravascular Measurement of Coronary Artery Flow Velocity," J. Doucette, et al., Circulation, vol. 85, pp. 1899–1911, May 1992.

"Advantages of Peak Velocity Over Mean Velocity Measurements Made by Doppler Catheters," S. Denardo et al., *Supplement I, Circulation*, vol. 86, No. 4, Abstract No. 3463, Oct. 1992.

"Clinical Applications of Doppler Coronary Flow Reserve Measurements," C. White, *Am J. Cardiology*, vol. 71, pp. 10D–16D, May 20, 1993.

"Applications of Coronary Flow Velocity During Angioplasty and Other Coronary Interventional Procedures," J. Segal, *Am J. Cardiology*, vol. 71, pp. 17D–25D, May 20, 1993.

"Assessment of Angiographically Intermediate Coronary Artery Stenosis Using the Doppler Flowire," M. Kern et al., *Am J. Cardiology*, vol. 71, pp. 26D–33D, May 20, 1993.

"Intracoronary Pressure and Flow Velocity with Sensor–Tip Guidewires: A New Methodologic Approach for Assessment of Coronary Hemodynamics Before and After Coronary Interventions," P. Serruys, et al., *Am J. Cardiology*, vol. 71, pp. 41D–53D, May 20, 1993.

"Intracoronary Blood Flow Velocity and Transstenotic Pressure Gradient Using Sensor–Tip Pressure and Doppler Guidewires: A New Technology for the Assessment of Stenosis Severit in the Catheterization Laboratory," C. Di Mario et al., *Catheterization and Cardiovascular Diagnosis* 28:311–319 (1993).

"Translesional Pressure–Flow Velocity Assessment in Patients: Part I," M. Kern et al., *Catheterization and Cardiovascular Diagnosis* 31:49–60 (1994).

"Pressure Guide .018"™ Guide wire–mounted pressure sensor for PTCA," 2–pg. brochure from RADI Medical Systems, date unknown.

FloWire® and FloMap® 2–pg. product brochure from Cardiometrics®, date unknown.

"Finally . . . Physiology in the Hands of the Cardiologist," 6–pg. product brochure from Cardiometrics®, date unknown.

"On the Spot—Sensor that Measures Blood Pressure," *New Scandinavian Technology*, 1–pg. article, date unknown.

"Reimbursement for Flow Velocity Studies with the Flowire," 6–pg. brochure from Cardiometrics®, date unknown.

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–25 is confirmed.

* * * * *